(12) United States Patent
Koseoglu et al.

(10) Patent No.: US 10,627,345 B2
(45) Date of Patent: *Apr. 21, 2020

(54) CHARACTERIZATION OF CRUDE OIL BY NEAR INFRARED SPECTROSCOPY

(71) Applicant: Saudi Arabian Oil Company, Dhahran (SA)

(72) Inventors: Omer Refa Koseoglu, Dhahran (SA); Adnan Al-Hajji, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 351 days.

This patent is subject to a terminal disclaimer.

(21) Appl. No.: 15/540,152

(22) PCT Filed: Jan. 5, 2016

(86) PCT No.: PCT/US2016/012171
§ 371 (c)(1),
(2) Date: Jun. 27, 2017

(87) PCT Pub. No.: WO2016/112004
PCT Pub. Date: Jul. 14, 2016

(65) Prior Publication Data
US 2018/0003627 A1    Jan. 4, 2018

Related U.S. Application Data

(60) Provisional application No. 62/099,704, filed on Jan. 5, 2015.

(51) Int. Cl.
G01N 21/359    (2014.01)
G01N 33/28     (2006.01)
G01N 21/3504   (2014.01)

(52) U.S. Cl.
CPC ....... *G01N 21/359* (2013.01); *G01N 21/3504* (2013.01); *G01N 33/2823* (2013.01); *G01N 2201/12* (2013.01)

(58) Field of Classification Search
None
See application file for complete search history.

(56) References Cited

U.S. PATENT DOCUMENTS

| 3,617,501 A | 11/1971 | Eng |
| 3,896,312 A | 7/1975 | Brown |

(Continued)

FOREIGN PATENT DOCUMENTS

| CA | 2781273 A1 | 12/2013 |
| EP | 0305090 A2 | 8/1988 |

(Continued)

OTHER PUBLICATIONS

I. Samfira in Characterization and Identity Confirmation of Essential Oils by Mid Infrared Absorption Pectrophotometry, 9 pages (Year: 2015).*

(Continued)

*Primary Examiner* — Tung S Lau
(74) *Attorney, Agent, or Firm* — Abelman, Frayne & Schwab

(57) ABSTRACT

A system and a method for determining one or more distillation temperatures for one or more given distillation weight percentages of a crude oil sample are provided, which can be used to produce a simulated distillation curve. Simulated distillation temperatures of crude oil samples are assigned as a function of density and data derived from direct near infrared spectroscopy measurement of the crude oil samples.

19 Claims, 3 Drawing Sheets

(56) References Cited

U.S. PATENT DOCUMENTS

| | | |
|---|---|---|
| 4,251,870 A | 2/1981 | Jaffe |
| 4,897,177 A | 1/1990 | Nadler |
| 4,971,915 A | 11/1990 | Schwartz et al. |
| 4,988,446 A | 1/1991 | Haberman |
| 5,121,337 A | 6/1992 | Brown |
| 5,223,714 A | 6/1993 | Maggard |
| 5,266,800 A | 11/1993 | Mullins |
| 5,304,807 A | 4/1994 | Lin |
| 5,424,959 A | 6/1995 | Reyes |
| 5,452,232 A | 9/1995 | Espinosa et al. |
| 5,475,612 A | 12/1995 | Espinosa |
| 5,490,085 A | 2/1996 | Lambert et al. |
| 5,572,030 A | 11/1996 | Ranson et al. |
| 5,600,134 A | 2/1997 | Ashe et al. |
| 5,602,755 A | 2/1997 | Ashe et al. |
| 5,656,810 A | 8/1997 | Alfano et al. |
| 5,699,269 A | 12/1997 | Ashe et al. |
| 5,699,270 A | 12/1997 | Ashe et al. |
| 6,070,128 A | 5/2000 | Descales |
| 6,258,987 B1 | 7/2001 | Schmidt et al. |
| 6,275,775 B1 | 8/2001 | Baco |
| 6,490,029 B1 | 12/2002 | Cho |
| 6,602,403 B1 | 8/2003 | Steffens et al. |
| 6,611,735 B1 | 8/2003 | Henly |
| 6,633,043 B2 | 10/2003 | Hegazi |
| 6,662,116 B2 | 12/2003 | Brown |
| 6,711,532 B1 | 3/2004 | Spieksma |
| 6,841,779 B1 | 1/2005 | Roehner et al. |
| 6,893,874 B2 | 5/2005 | Stark |
| 7,126,332 B2 | 10/2006 | Blanz |
| 7,173,239 B2 | 2/2007 | DiFoggio |
| 7,560,711 B2 | 7/2009 | Hegazi |
| 7,598,487 B2 | 10/2009 | Qian |
| 8,714,246 B2 | 5/2014 | Pop et al. |
| 8,930,149 B1 | 1/2015 | Koseoglu et al. |
| 9,285,307 B2 | 3/2016 | Koseoglu et al. |
| 9,423,391 B2 | 8/2016 | Koseoglu et al. |
| 9,429,556 B2 | 8/2016 | Koseoglu et al. |
| 9,778,240 B2 | 10/2017 | Koseoglu et al. |
| 9,816,919 B2 | 11/2017 | Koseoglu et al. |
| 2002/0052769 A1 | 5/2002 | Navani et al. |
| 2003/0141459 A1 | 7/2003 | Hegazi et al. |
| 2003/0195708 A1 | 10/2003 | Brown |
| 2005/0109934 A1 | 5/2005 | David |
| 2005/0173298 A1 | 8/2005 | Wellington |
| 2006/0043004 A1 | 3/2006 | Rose |
| 2006/0047444 A1 | 3/2006 | Brown |
| 2006/0142955 A1 | 6/2006 | Jones |
| 2007/0050154 A1* | 3/2007 | Albahri ............... G01N 25/14 |
| | | 702/22 |
| 2007/0231912 A1 | 10/2007 | Reischman et al. |
| 2007/0295640 A1 | 12/2007 | Tan et al. |
| 2008/0037006 A1 | 2/2008 | Canas Triana |
| 2008/0040051 A1 | 2/2008 | Franklin et al. |
| 2008/0206887 A1 | 8/2008 | Chen |
| 2008/0248967 A1 | 10/2008 | Butler et al. |
| 2008/0253426 A1 | 10/2008 | Voelkening |
| 2008/0260584 A1 | 10/2008 | Gudde et al. |
| 2009/0003853 A1* | 1/2009 | Hatakeyama ...... G03G 21/0094 |
| | | 399/34 |
| 2009/0011517 A1 | 1/2009 | Hodges |
| 2009/0180949 A1 | 7/2009 | Cui |
| 2009/0279072 A1 | 11/2009 | Arakawa |
| 2009/0290144 A1 | 11/2009 | Hegazi |
| 2009/0316139 A1 | 12/2009 | Shrestha |
| 2010/0049681 A1 | 2/2010 | Pradhan |
| 2010/0113311 A1 | 5/2010 | Eccleston et al. |
| 2010/0204925 A1 | 8/2010 | Albahri |
| 2010/0211329 A1 | 8/2010 | Farquharson et al. |
| 2010/0218585 A1 | 9/2010 | Chawla |
| 2011/0152136 A1 | 6/2011 | Hughes et al. |
| 2011/0308996 A1 | 12/2011 | Choudhary |
| 2012/0171151 A1 | 7/2012 | Thomassian |
| 2014/0075827 A1 | 3/2014 | Gonzalez et al. |
| 2014/0156241 A1 | 6/2014 | Kumar et al. |
| 2015/0106027 A1 | 4/2015 | Koseoglu et al. |
| 2015/0106028 A1 | 4/2015 | Koseoglu et al. |
| 2015/0106029 A1 | 4/2015 | Koseoglu et al. |
| 2015/0106031 A1* | 4/2015 | Koseoglu ........... G01N 21/3577 |
| | | 702/24 |
| 2015/0112610 A1 | 4/2015 | Koseoglu |
| 2015/0112611 A1 | 4/2015 | Koseoglu |
| 2016/0011102 A1 | 1/2016 | Koseoglu et al. |
| 2016/0187253 A1 | 6/2016 | Koseoglu et al. |
| 2016/0195481 A1 | 7/2016 | Koseoglu |
| 2016/0195507 A1 | 7/2016 | Koseoglu |
| 2016/0195508 A1 | 7/2016 | Al-Hajji |
| 2016/0377589 A1 | 12/2016 | Koseoglu |
| 2017/0003217 A1 | 1/2017 | Koseoglu |
| 2017/0363540 A1 | 12/2017 | Koseoglu |
| 2017/0363591 A1 | 12/2017 | Koseoglu |
| 2017/0363602 A1 | 12/2017 | Koseoglu |
| 2017/0363603 A1 | 12/2017 | Koseoglu |
| 2017/0370830 A1* | 12/2017 | Koseoglu ........... G01N 33/2823 |

FOREIGN PATENT DOCUMENTS

| | | | |
|---|---|---|---|
| EP | 0304232 A2 | 2/1989 | |
| EP | 0552300 A1 | 7/1993 | |
| EP | 0794433 A1 | 9/1997 | |
| EP | 0859236 A1 | 8/1998 | |
| EP | 0984277 A1 | 3/2000 | |
| EP | 0 984 277 * | 8/2000 | ............ G01N 30/86 |
| SU | 817486 A1 | 3/1981 | |
| SU | 1523972 A1 | 11/1989 | |
| WO | 03/048759 A1 | 6/2003 | |
| WO | 2004033513 A2 | 4/2004 | |
| WO | 2006030218 A1 | 3/2006 | |
| WO | 2009082418 A2 | 7/2009 | |
| WO | 2013102916 A1 | 7/2013 | |
| WO | WO 2016/112004 * | 6/2016 | ............ G01N 21/359 |
| WO | WO 2016/111982 * | 7/2016 | ............ G01N 21/359 |

OTHER PUBLICATIONS

Adhvaryu, A. et al., Quantitative NMR Spectroscopy for the Prediction of Base Oil Properties, Tribology Transactions, vol. 43, No. 2, 2000, pp. 245-250.

Albahri, T. et al, Octane Number and Aniline Point of Petroleum Fuels, 2002, Fuel Chemistry Division, vol. 47(2), pp. 710-711.

Ali, M., Resolution and Quantification of Ring Type Aromatics by HPLC Method using N-Hexane Elution, 2003, King Fahd University of Petroleum and Minerals, pp. 1-9.

ASTM D2887-01, Standard Test Method for Boiling Range Distribution of Petroleum Fractions by Gas Chromatography, Annual Book of ASTM Standards, vol. 14, No. 02, pp. 204-216.

Birch C., Oil & Gas Journal, Jan. 14, 2002, pp. 54-59 (printed Jul. 9, 2014 from http://www.ogj.com/articles/print/volume-100/issue-2/processing/achieving-maximum-crude-oil-value-depends-on-accurate-evaluation.html).

Bowden, J. et al., Octane-Cetane Relationship, 1974, NTIS, p. 8.

Chemstations, Inc., Physical Properties User's Guide, 2004, Chemstations Inc., Ver. 5.4, pp. 18-22.

Cookson, D.J. et al., Investigation of the Chemical Basis of Diesel Fuel Properties, Energy & Fuels, 1988, vol. 2, No. 6, pp. 854-860.

Duvekot, C., Fast Analysis of Paraffins, iso-Paraffins, Olefins, iso-Olefins, Naphthenes and Aromatics in Hydrocarbon Streams, Varian, Inc., 2008, pp. 1-4.

Evokimov, I, et al, Potential of UV-Visible Absorption Spectroscopy for characterizing Crude Petroleum Oils, Oil an Gas Business, 2007, 21 pages.

Falla, F, et al., Characterization of crude petroleum by NIR, Journal of Petroleum Science and Engineering, vol. 51, 2006, pp. 127-137.

Fernandez-Lima, F. et al., Petroleum Crude Oil Characterization by IMS-MS and FTICR MS, 2009, American Chemical Society, Ed. 81, pp. 9941-9945.

Grizzle, P. et al., Automated Liquid Chromatographic Compound Class Group-Type Separation of Crude Oils and Bitumens Using Chemically Bonded Aminolilane, 1986, Publisher Anal. Chem., vol. 58, pp. 2389-2390.

(56) References Cited

OTHER PUBLICATIONS

Hasan, M.U. et al., Structural characterization of Saudi Arabian heavy crude oil by n.m.r. spectroscopy, Fuel, vol. 62, 1983, pp. 518-523.

Hidajat, K, et al., Quality characterisation of crude oils by partial least square calibration of NIR spectral profiles, Near Infrared Spectrosc, vol. 8, pp. 53-59, 2000.

Jokuty, P. et al., Hydrocarbon Groups and Their Relationships to Oil Properties and Behavior, 1995, Published by Whiticar Scientific, p. 11.

Khanmohammadi, M, et al., Characterization of petroleum-based products by infrared spectroscopyu and chemometrics, Trac Trends in Analytical Chem, vol. 35, 2012.

Kok, M, et al., High pressure TGA analysis of crude oils, Thermochimica Acta., vol. 287, No. 1, 1996, pp. 91-99.

Mckenna, Amy M., Heavy Petroleum Composition. 1. Exhaustive Compositional Analysis of Athabasca Bitumen HVGO Distillates by Fourier Transform Ion Cyclotron Resonance Mass Spectrometry: A Definitive Test of the Boduszynski Model, Energy Fuels, 24, 2010, pp. 2929-2038.

Mohammed, S., The Use of Compounds Chemically Related to Analyte as Surrogate Reference Standards in Quantitative HPLC, Feb. 2008, Produced by Kwame Nkrumah University of Science and Technology, Kumasi, p. 16.

Pande, S., et al., Cetana Number Predictions of a Trial Index Based on Compositional Analysis, American Chemical Society, 1989, pp. 308-312.

Patra, D, et al, Determination of Synchronous Fluorescence Scan Parameters for Certain Petroleum Products, Journal of Scientific & Industrial Research, Apr. 1, 2000, pp. 300-305.

Pavlovic K., Oil & Gas Journal, Nov. 22, 1999, pp. 51-56 (printed Jul. 9, 2014 from http://www.ogj.com/articles/print/volume-97/issue-47/in-this-issue/refining/gravity-and-sulfur-based-crude-valuations-more-accurate-than-believed.html).

Pereira,Thieres M. C., An evaluation of the aromaticity of asphaltenes using atmospheric pressure photoionization Fourier transform ion cyclotron resonance mass spectrometry—APP (±) FT-ICR MS, Fuel, 2014, vol. 118, 2014, pp. 348-357.

Rodgers, R. et al., Advanced Characterization of Petroleum Crude and Products by High Field Fourier Transform Ion Cyclotron Resonance Mass Spectrometry, 2002, Fuel Chemistry Division, Ed. 47(2), pp. 636-637.

Shea, T.M., Modeling Base Oil Properties using NMR Spectroscopy and Neural Networks, Tribology Transactions, vol. 46, No. 3, 2003, pp. 296-302.

Souza, C. et al., Cetane Number Assessment in Diesel Fuel by 1H or Hydrogen Nuclear Magnetic Resonance-Based Multivariate Calibration, Energy & Fuels, vol. 28, 2014, pp. 4958-4962.

Speight, Handbook of Petroleum Product Analysis, 2002.

Terra, L. et al., Petroleomics by electrospray ionization FT-ICR mass spectrometry coupled to partial least squares with variable selection methods: prediction of the total acid number of crude oils, 2014, Analyst, vol. 139, 2014, pp. 4908-4916.

University of Oldenburg, Institute of Physics, Catalogue of Optical Spectra of Oils, Jan. 2005, retrieved from http://las.physik.uni-oldenburg.de/data/spectra/indez.htm, 6 pages.

Yamashita, G.T., Evaluation of Integration Procedures for PNA Analysis by C-13 NMR, Symposium on Analytical Chemistry of Heavy Oils/Resids Presented Before the Division of Petroleum Chemistry, Inc., American Chemical Society, Dallas Meeting, Apr. 9-14, 1989, pp. 301-305.

PCT/US2016/012171, International Search Report and Written Opinion dated Apr. 20, 2016, 13 pages.

\* cited by examiner

CHARACTERIZATION OF CRUDE OIL BY NEAR INFRARED SPECTROSCOPY

RELATED APPLICATIONS

This application claims the benefit of U.S. Provisional Patent Application No. 62/099,704 filed Jan. 5, 2015, the disclosure of which is hereby incorporated by reference.

FIELD OF THE INVENTION

This invention relates to a method and process for the evaluation of samples of crude oil and its fractions by near infrared spectroscopy.

BACKGROUND OF THE INVENTION

Crude oil originates from the decomposition and transformation of aquatic, mainly marine, living organisms and/or land plants that became buried under successive layers of mud and silt some 15-500 million years ago. They are essentially very complex mixtures of many thousands of different hydrocarbons. Depending on the source, the oil predominantly contains various proportions of straight and branched-chain paraffins, cycloparaffins, and naphthenic, aromatic, and polynuclear aromatic hydrocarbons. These hydrocarbons can be gaseous, liquid, or solid under normal conditions of temperature and pressure, depending on the number and arrangement of carbon atoms in the molecules.

Crude oils vary widely in their physical and chemical properties from one geographical region to another and from field to field. Crude oils are usually classified into three groups according to the nature of the hydrocarbons they contain: paraffinic, naphthenic, asphaltic, and their mixtures. The differences are due to the different proportions of the various molecular types and sizes. One crude oil can contain mostly paraffins, another mostly naphthenes. Whether paraffinic or naphthenic, one can contain a large quantity of lighter hydrocarbons and be mobile or contain dissolved gases; another can consist mainly of heavier hydrocarbons and be highly viscous, with little or no dissolved gas. Crude oils can also include heteroatoms containing sulfur, nitrogen, nickel, vanadium and other elements in quantities that impact the refinery processing of the crude oil fractions. Light crude oils or condensates can contain sulfur in concentrations as low as 0.01 W %; in contrast, heavy crude oils can contain as much as 5-6 W %. Similarly, the nitrogen content of crude oils can range from 0.001-1.0 W %.

The nature of the crude oil governs, to a certain extent, the nature of the products that can be manufactured from it and their suitability for special applications. A naphthenic crude oil will be more suitable for the production of asphaltic bitumen, a paraffinic crude oil for wax. A naphthenic crude oil, and even more so an aromatic one, will yield lubricating oils with viscosities that are sensitive to temperature. However, with modern refining methods there is greater flexibility in the use of various crude oils to produce many desired type of products.

A crude oil assay is a traditional method of determining the nature of crude oils for benchmarking purposes. Crude oils are subjected to true boiling point (TBP) distillations and fractionations to provide different boiling point fractions. The crude oil distillations are carried out using the American Standard Testing Association (ASTM) Method D 2892. The common fractions and their nominal boiling points are given in Table 1.

TABLE 1

| Fraction | Boiling Point, ° C. |
| --- | --- |
| Methane | −161.5 |
| Ethane | −88.6 |
| Propane | −42.1 |
| Butanes | −6.0 |
| Light Naphtha | 36-90 |
| Mid Naphtha | 90-160 |
| Heavy Naphtha | 160-205 |
| Light Gas Oil | 205-260 |
| Mid Gas Oil | 260-315 |
| Heavy Gas Oil | 315-370 |
| Light Vacuum Gas Oil | 370-430 |
| Mid Vacuum Gas Oil | 430-480 |
| Heavy Vacuum Gas oil | 480-565 |
| Vacuum Residue | 565+ |

The yields, composition, physical and indicative properties of these crude oil fractions, where applicable, are then determined during the crude assay work-up calculations. Typical compositional and property information obtained from a crude oil assay is given in Table 2.

TABLE 2

| Property | Unit | Property Type | Fraction |
| --- | --- | --- | --- |
| Yield Weight and Volume % | W % | Yield | All |
| API Gravity | ° | Physical | All |
| Viscosity Kinematic @ 38° C. | ° | Physical | Fraction boiling >250° C. |
| Refractive Index @ 20° C. | Unitless | Physical | Fraction boiling <400° C. |
| Sulfur | W % | Composition | All |
| Mercaptan Sulfur, W % | W % | Composition | Fraction boiling <250° C. |
| Nickel | Ppmw | Composition | Fraction boil ing >400° C. |
| Nitrogen | Ppmw | Composition | All |
| Flash Point, COC | ° C. | Indicative | All |
| Cloud Point | ° C. | Indicative | Fraction boiling >250° C. |
| Pour Point, (Upper) | ° C. | Indicative | Fraction boiling >250° C. |
| Freezing Point | ° C. | Indicative | Fraction boiling >250° C. |
| Microcarbon Residue | W % | Indicative | Fraction boiling >300° C. |
| Smoke Point, mm | mm | Indicative | Fraction boiling between 150-250 |
| Cetane Index | Unitless | Indicative | Fraction boiling between 150-400 |
| Aniline Point | ° C. | Indicative | Fraction boiling <520° C. |

Due to the number of distillation cuts and the number of analyses involved, the crude oil assay work-up is both costly and time consuming.

In a typical refinery, crude oil is first fractionated in the atmospheric distillation column to separate sour gas and light hydrocarbons, including methane, ethane, propane, butanes and hydrogen sulfide, naphtha (36°-180° C.), kerosene (180°-240° C.), gas oil (240°-370° C.) and atmospheric residue (>370° C.). The atmospheric residue from the atmospheric distillation column is either used as fuel oil or sent to a vacuum distillation unit, depending on the configuration of the refinery. The principal products obtained from vacuum distillation are vacuum gas oil, comprising hydrocarbons boiling in the range 370°-520° C., and vacuum residue, comprising hydrocarbons boiling above 520° C. Crude assay data is conventionally obtained from individual analysis of these cuts to help refiners to understand the general composition of the crude oil fractions and properties so that the fractions can be processed most efficiently and effectively in an appropriate refining unit. Indicative properties are used to determine the engine/fuel performance or usability or flow characteristic or composition. A summary of the indicative properties and their determination methods with description is given below.

Viscosity is a measure of the resistance of a fluid which is being deformed by either shear stress or tensile stress. Viscosity describes a fluid's internal resistance to flow and may be thought of as a measure of fluid friction. All real fluids (except superfluids) have some resistance to stress, but a fluid which has no resistance to shear stress is known as an ideal fluid or inviscid fluid. Viscosity of many petroleum fuels is important for the estimation of process units, optimum storage, handling, and operational conditions and determined by ASTM method D445.

The cetane number of diesel fuel oil, determined by the ASTM D613 method, provides a measure of the ignition quality of diesel fuel; as determined in a standard single cylinder test engine; which measures ignition delay compared to primary reference fuels. The higher the cetane number; the easier the high-speed; direct-injection engine will start; and the less white smoking and diesel knock after start-up are. The cetane number of a diesel fuel oil is determined by comparing its combustion characteristics in a test engine with those for blends of reference fuels of known cetane number under standard operating conditions. This is accomplished using the bracketing hand wheel procedure which varies the compression ratio (hand wheel reading) for the sample and each of the two bracketing reference fuels to obtain a specific ignition delay, thus permitting interpolation of cetane number in terms of hand wheel reading.

The cloud point, determined by the ASTM D2500 method, is the temperature at which a cloud of wax crystals appears when a lubricant or distillate fuel is cooled under standard conditions. Cloud point indicates the tendency of the material to plug filters or small orifices under cold weather conditions. The specimen is cooled at a specified rate and examined periodically. The temperature at which cloud is first observed at the bottom of the test jar is recorded as the cloud point. This test method covers only petroleum products and biodiesel fuels that are transparent in 40 mm thick layers, and with a cloud point below 49° C.

The pour point of petroleum products, determined by the ASTM D97 method, is an indicator of the ability of oil or distillate fuel to flow at cold operating temperatures. It is the lowest temperature at which the fluid will flow when cooled under prescribed conditions. After preliminary heating, the sample is cooled at a specified rate and examined at intervals of 3° C. for flow characteristics. The lowest temperature at which movement of the specimen is observed is recorded as the pour point.

The aniline point, determined by the ASTM D611 method, is the lowest temperature at which equal volumes of aniline and hydrocarbon fuel or lubricant base stock are completely miscible. A measure of the aromatic content of a hydrocarbon blend is used to predict the solvency of a base stock or the cetane number of a distillate fuel Specified volumes of aniline and sample, or aniline and sample plus n-heptane, are placed in a tube and mixed mechanically. The mixture is heated at a controlled rate until the two phases become miscible. The mixture is then cooled at a controlled rate and the temperature at which two phases separate is recorded as the aniline point or mixed aniline point.

To determine these properties of gas oil or naphtha fractions conventionally, these fractions have to be distilled off from the crude oil and then measured/determined using various analytical methods that are laborious, costly and time consuming.

Infrared energy is the electromagnetic energy of molecular vibration. The energy band is defined for convenience as the near infrared (0.78-2.50 microns), the infrared (or mid-infrared) 2.50-40.0 microns, and the far infrared (40.0-1000 microns).

New rapid and direct methods to help better understand crude oil composition and properties from analysis of whole crude oil will save producers, marketers, refiners and/or other crude oil users substantial expense, effort and time. Therefore, a need exists for an improved system and method for determining indicative properties of crude oil fractions from different sources.

SUMMARY OF THE INVENTION

Systems and methods for assigning one or more distillation temperatures for one or more given distillation weight percentages of a crude oil sample are provided, which can be used to produce a simulated distillation curve. Simulated distillation temperatures of crude oil samples are assigned as a function of density and data derived from direct near infrared spectroscopy measurement of the crude oil samples. The correlations also provide information about the gas oil indicative properties without fractionation/distillation (crude oil assays) and will help producers, refiners, and marketers to benchmark the oil quality and, as a result, valuate the oils without performing the customary extensive and time-consuming crude oil assays.

BRIEF DESCRIPTION OF THE DRAWING

Further advantages and features of the present invention will become apparent from the following detailed description of the invention when considered with reference to the accompanying drawings, in which.

DETAILED DESCRIPTION OF INVENTION

A system and method is provided for determining distillation data of a hydrocarbon sample. The systems and methods are applicable for naturally occurring hydrocarbons derived from crude oils, bitumens, heavy oils, shale oils and from refinery process units including hydrotreating, hydroprocessing, fluid catalytic cracking, coking, and visbreaking or coal liquefaction. Samples can be obtained from various sources, including an oil well, stabilizer, extractor, or distillation tower.

A method for determining boiling point distribution of a hydrocarbon oil based upon near infrared spectroscopy data derived from a sample of the hydrocarbon oil and the density of the sample is provided. The sample is prepared for near infrared spectroscopy analysis. Spectra data for the sample is obtained by a near infrared spectroscopy analysis. The spectra data obtained by near infrared spectroscopy analysis of the sample is entered into the computer. Cumulative near infrared absorbance of the hydrocarbon oil is calculated from the near infrared spectroscopy data. Cumulative near infrared absorbance of the hydrocarbon oil is normalized to 100 W %. The wavenumber is determined at 0.5, 5, 10, 20, 30, 40, 50, 60, 70, 80, 90, 95, 99.5 W % points. Boiling point distribution of hydrocarbon oil is calculated from normalized near infrared data and the density of hydrocarbon oil. The wavenumber of near infrared spectrum can be in the range 4,000-12,821 cm-1.

Figure 1:
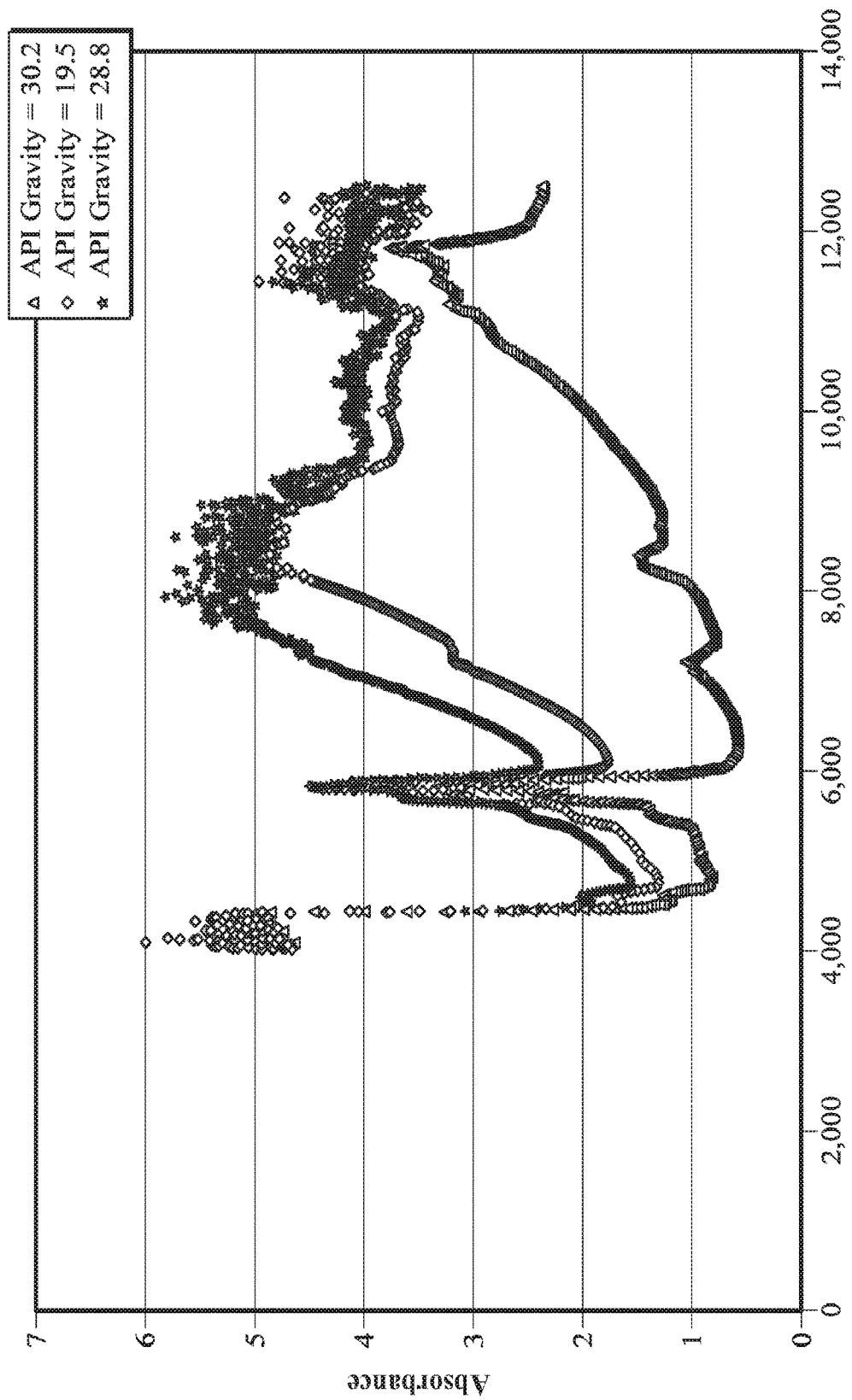
FIG. 1 is a graphic plot of typical near infrared spectroscopy data for three types of crude oil.

In the system and method herein, spectra are obtained by a suitable known or to be developed near infrared spectroscopy techniques, for instance, to obtain graphic plots of near infrared spectroscopy data as shown in FIG. 1. Infrared energy is the electromagnetic energy of molecular vibration. The energy band is defined for convenience as the near infrared (0.78-2.50 microns), the infrared (or mid-infrared) 2.50-40.0 microns, and the far infrared (40.0-1000 microns). However, even though official standards, textbooks, and the scientific literature generally state that the NIR spectral region extends from 780-2500 nanometers (12821-4000 cm-1), a simple set of liquid phase hydrocarbon spectra demonstrates that the vibrational information characterized by the harmonic vibrations of the C—H stretch fundamental and their corresponding combination bands occurs from approximately 690-3000 nm. The predominant near-infrared spectral features include: the methyl C—H stretching vibrations, methylene C—H stretching vibrations, aromatic C—H stretching vibrations, and O—H stretching vibrations. Minor but still important spectral features include: methoxy C—H stretching, carbonyl associated C—H stretching; N—H from primary amides, secondary amides (both alkyl, and aryl group associations), N—H from primary, secondary, and tertiary amines, and N—H from amine salts.

Qualitative and quantitative near infrared (NIR) spectroscopic methods typically require the application of multivariate calibration algorithms and statistical methods (i.e. chemometrics) to model NIR spectral response to chemical or physical properties of the samples used for calibration. The NIR method relies on the spectra-structure correlations existing between a measured spectral response caused by the harmonics of the fundamental vibrations occurring at infrared frequencies. These harmonic vibrations occur at unique frequencies depending upon the quantity of absorber (analyte), type of absorbing molecules present within the sample, and the sample thickness. Quantitative methods are possible where changes in the response of the near infrared spectrometer are proportional to changes in the concentration of chemical components, or in the physical characteristics (scattering/absorptive properties) of samples undergoing analysis Near infrared spectroscopy is used where multicomponent molecular vibrational analysis is required in the presence of interfering substances. The near infrared spectra consist of overtones and combination bands of the fundamental molecular absorptions found in the mid infrared region. Near infrared spectra consist of generally overlapping vibrational bands that may appear non-specific and poorly resolved. The use of chemometric mathematical data processing and multiple harmonics can be used to calibrate for qualitative of quantitative analysis despite these apparent spectroscopic limitations. Traditional near infrared spectroscopy has been most often used for analysis of lignin polymers (2270 nm), paraffins and long alkane chain polymers (2310 nm), glucose based polymers such as cellulose (2336 nm), amino acid polymers as proteins (2180 nm), carbohydrates (2100 nm), and moisture (1440 and 1940 nm). When analyzing synthetic and natural materials NIR spectroscopy has shown unprecedented industrial success in multiple applications. The basic uses of near infrared spectroscopy have been for process control, quality assessment, identification of raw materials and process byproducts, and chemical quantitative analysis of complex mixtures.

Note that a near infrared spectrum consists in the convolution of the measuring instrument function with the unique optical characteristics of the sample being measured (i.e. the sample is an active optical element of the spectrometer). The reference values are those chemical or physical parameters to be predicted using the NIR spectroscopic measurements. A spectrum may, or may not, contain information related to the sample chemistry measured using any specific reference method. Spectra-structure correlation provides a basis for the establishment of a known cause and effect relationship between instrument response and reference (analyte) data, in order to provide a more scientific basis for multivariate-based near infrared spectroscopy. When performing multivariate calibrations, analytically valid calibration models require a relationship between X (the instrument response data or spectrum), and Y (the reference data). The use of probability alone tells us only if X and Y 'appear' to be related. If no cause-effect relationship exists between spectra-structure correlation and reference values the model will have no true predictive importance. Thus, knowledge of cause and effect creates a basis for scientific decision-making.

Factors affecting the integrity of the teaching samples used to calibrate spectrophotometers for individual NIR applications include the variations in sample chemistry, the physical condition of samples, and the measurement conditions. Teaching Sets must represent several sample 'spaces' to include: compositional space, instrument space, and measurement condition (sample handling and presentation) space. Interpretive spectroscopy is a key intellectual process in approaching NIR measurements if one is to achieve an analytical understanding of these measurements.

Near-infrared (NIR) spectroscopy has been employed for the characterization of products derived from petroleum, such as gasoline and diesel fuel, with considerable success. The intrinsic capacity of the NIR spectrum to obtain information on the different types of C—H bonds as well as other chemical bonds of interest (such as S—H and N—H) has been proved to be valuable in the prediction of quality parameters such as octane number, ethanol content, MTBE (methyl tert-butyl ether) content, distillation points, Reid vapor pressure and aromatic and saturated contents in gasoline. The information present in the NIR spectrum can be successfully applied to assign quality parameters for gas oil fractions such as cetane number, pour point, cloud point and aniline point.

Figure 2:
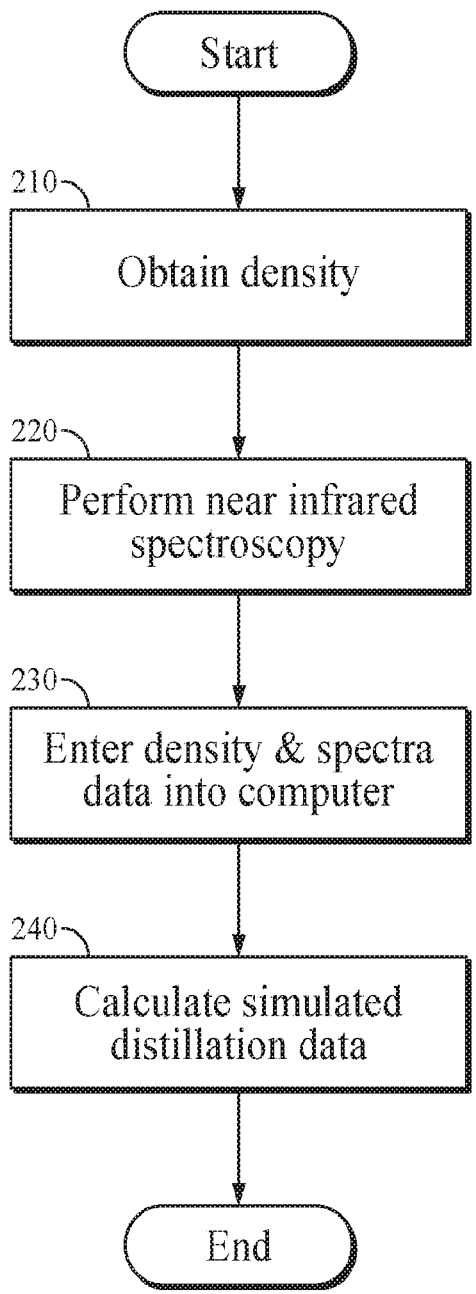
FIG. 2 is a process flow diagram of steps carried out to characterize distillation data of a crude oil sample, using the system and method herein.

FIG. 2 shows a process flowchart of steps in a method according to one embodiment herein. In step 210, a crude oil sample is weighed and its density obtained. In step 220, crude oils were analyzed by near infrared spectroscopy, e.g., in accordance with the instructions of the equipment manufacturer. No dilution or special preparation is required.

In step 230, the density and spectra data are entered into a computer.

In step 240, the distillation temperature at a given distillation weight percentage is calculated as a function of the wavenumber at known weight percent absorbance values and the density.

Equation (1) is used to calculate and assign a distillation temperature for a given distillation weight percentage:

$$T_{DT} = K_{SD} + X1_{SD}\left(\frac{1}{NIRWN}\right) + \quad (1)$$
$$X2_{SD}\left(\frac{1}{DEN}\right) + X3_{SD}\left(\frac{1}{NIRWN^2}\right) + X4_{SD}\left(\frac{1}{DEN^2}\right) +$$
$$X5_{SD}\left(\frac{1}{NIRWN*DEN}\right)X6_{SD}\left(\frac{1}{NIRWN^3}\right) + X7_{SD}\left(\frac{1}{DEN^3}\right) +$$
$$X8_{SD}\left(\frac{1}{NIRWN^2*DEN}\right) + X9_{SD}\left(\frac{1}{DEN^2*NIRWN}\right);$$

where:

DT is the distillation weight percentage, $K_{SD}$, $X1_{SD}$, $X2_{SD}$, $X3_{SD}$, $X4_{SD}$, $X5_{SD}$, $X6_{SD}$, $X7_{SD}$, $X8_{SD}$ and $X9_{SD}$ are constants, DEN is the density of the sample (kg/L), and NIRWN is the wavenumber at DT.

Figure 3:
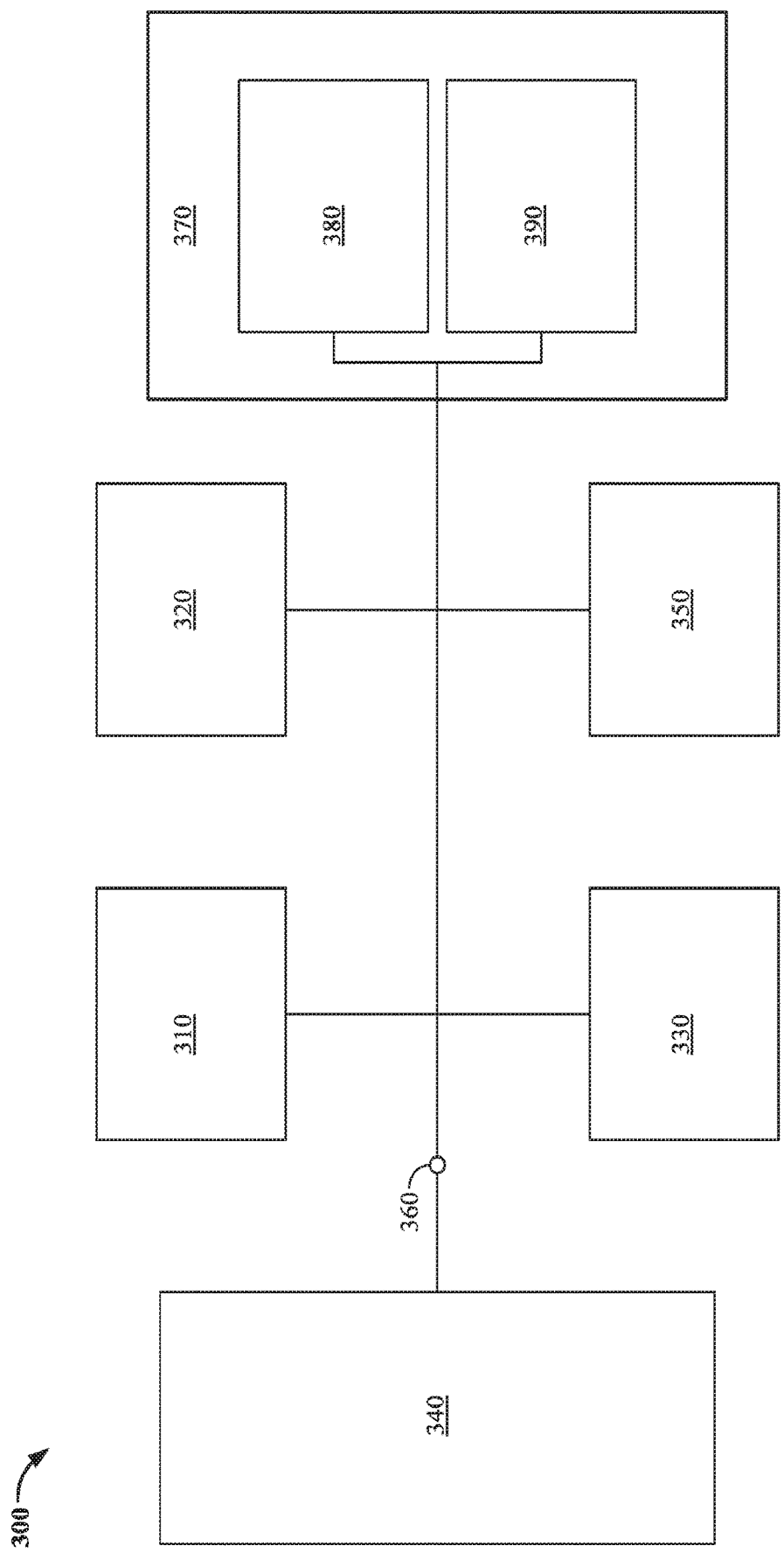
FIG. 3 is a block diagram of a component of a system for implementing the invention, according to one embodiment.

An exemplary block diagram of a computer system 300 by which simulated distillation data calculation modules can be implemented is shown in FIG. 3. Computer system 300 includes a processor 310, such as a central processing unit, an input/output interface 320 and support circuitry 330. In certain embodiments, where the computer 300 requires direct human interaction, a display 340 and an input device 350 such as a keyboard, mouse or pointer are also provided. The display 340, input device 350, processor 310, input/output interface 320 and support circuitry 330 are shown connected to a bus 360 which also connects to a memory unit 370. Memory 370 includes program storage memory 380 and data storage memory 390. Note that while computer 300 is depicted with the direct human interface components of display 340 and input device 350, programming of modules and importation and exportation of data can also be accomplished over the interface 320, for instance, where the computer 300 is connected to a network and the programming and display operations occur on another associated computer, or via a detachable input device, as are well known in the art for interfacing programmable logic controllers.

Program storage memory 380 and data storage memory 390 can each comprise volatile (RAM) and non-volatile (ROM) memory units and can also comprise hard disk and backup storage capacity, and both program storage memory 380 and data storage memory 390 can be embodied in a single memory device or separated in plural memory devices. Program storage memory 380 stores software program modules and associated data, and in particular stores calculation module(s) for obtaining the simulated distillation data. Data storage memory 390 stores data used and/or generated by the one or more modules of the present invention, including density of the oil sample, NIR spectroscopy data or portions thereof used by the one or more modules of the present system, and calculated data generated by the one or more modules of the present system.

The calculated and assigned results in accordance with the systems and methods herein are displayed, audibly outputted, printed, and/or stored to memory for use as described herein.

It is to be appreciated that the computer system 300 can be any general or special purpose computer such as a personal computer, minicomputer, workstation, mainframe, a dedicated controller such as a programmable logic controller, or a combination thereof. While the computer system 300 is shown, for illustration purposes, as a single computer unit, the system can comprise a group/farm of computers which can be scaled depending on the processing load and database size, e.g., the total number of samples that are processed and results maintained on the system. The computer system 300 can serve as a common multi-tasking computer.

The computing device 300 preferably supports an operating system, for example, stored in program storage memory 390 and executed by the processor 310 from volatile memory. According to the present system and method, the operating system contains instructions for interfacing the device 300 to the calculation module(s). According to an embodiment of the invention, the operating system contains instructions for interfacing computer system 300 to the Internet and/or to private networks.

EXAMPLE

A sample of Arabian medium crude with a density of 0.8828 Kg/l was analyzed by near infrared spectroscopy. The spectra data, which was obtained in the wavenumber range 4,000-12,821, is presented in Table 3 and is shown in FIG. 1 as the sample with an API gravity of 28.8°. Cumulative near infrared absorbance of the sample was calculated from the near infrared spectroscopy data and normalized; a summary of absorbances versus wavenumber was obtained using interpolation and/or numerical methods as follows:

5 W %=1.2091*1e-4 cm-1; 10 W %=1.1721*1e-4 cm-1; 20 W %=1.0978*1e-4 cm-1; 30 W %=1.0185*1e-4 cm-1; 40 W %=0.9405*1e-4 cm-1; 50 W %=0.8747*1e-4 cm-1; 60 W %=0.8161*1e-4 cm-1; 70 W %=0.7407*1e-4 cm-1; 80 W %=0.6268*1e-4 cm-1.

The simulated distillation curve was obtained using Equation 1. The following constant values were used to predict the temperature at 50 W % point, obtained by linear regression:

$K_{SD}$=3.74721865E+04

$X1_{SD}$=5.72117464E+04

$X2_{SD}$=4.50736562E+04

$X3_{SD}$=5.83590589E+03

$X4_{SD}$=1.79172881E+04

$X5_{SD}$=1.18035802E+05

$X6_{SD}$=3.99969439E+02

$X7_{SD}$=2.37278141E+04

$X8_{SD}$=3.18900766E+03

$X9_{SD}$=5.63368697E+04

Using the above constants at a distillation weight percentage DT of 50%, the simulated distillation temperature at 50% distillation weight percentage is calculated and assigned as 412.4° C. The temperatures at 0.5, 5, 10, 20, 30, 40, 50, 60, 70, 80 W % points are calculated and compared with the actual data, and a perfect fit was obtained.

In alternate embodiments, the present invention can be implemented as a computer program product for use with a computerized computing system. Those skilled in the art will readily appreciate that programs defining the functions of the present invention can be written in any appropriate programming language and delivered to a computer in any form, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the system embodiments can incorporate a variety of computer readable media that comprise a computer usable medium having computer readable code means embodied therein. One skilled in the art will recognize that the software associated with the various processes described can be embodied in a wide variety of computer accessible media from which the software is loaded and activated. Pursuant to In re *Beauregard*, 35 USPQ2d 1383 (U.S. Pat. No. 5,710,578), the present invention contemplates and includes this type of computer readable media within the scope of the invention. In certain embodiments, pursuant to In re *Nuijten*, 500 F.3d 1346 (Fed. Cir. 2007) (U.S. patent application Ser. No. 09/211,928), the scope of the present claims is limited to computer readable media, wherein the media is both tangible and non-transitory.

The system and method of the present invention have been described above and with reference to the attached figure; however, modifications will be apparent to those of ordinary skill in the art and the scope of protection for the invention is to be defined by the claims that follow.

TABLE 3

| $cm^{-1}$ | Absorb. |
|---|---|
| 12493 | 3.61 |
| 12489 | 3.56 |
| 12485 | 3.52 |
| 12482 | 3.48 |
| 12478 | 3.51 |
| 12474 | 3.56 |
| 12470 | 3.57 |
| 12466 | 3.56 |
| 12462 | 3.58 |
| 12458 | 3.6 |
| 12455 | 3.6 |
| 12451 | 3.65 |
| 12447 | 3.74 |
| 12443 | 3.72 |
| 12439 | 3.68 |
| 12435 | 3.67 |
| 12431 | 3.63 |
| 12428 | 3.6 |
| 12424 | 3.57 |
| 12420 | 3.51 |
| 12416 | 3.5 |
| 12412 | 3.57 |
| 12408 | 3.59 |
| 12404 | 3.54 |
| 12401 | 3.57 |
| 12397 | 3.68 |
| 12393 | 3.7 |
| 12389 | 3.63 |
| 12385 | 3.58 |
| 12381 | 3.58 |
| 12377 | 3.57 |
| 12374 | 3.57 |
| 12370 | 3.57 |
| 12366 | 3.56 |
| 12362 | 3.55 |
| 12358 | 3.56 |
| 12354 | 3.56 |
| 12350 | 3.54 |
| 12347 | 3.51 |
| 12343 | 3.5 |
| 12339 | 3.53 |
| 12335 | 3.6 |

TABLE 3-continued

| $cm^{-1}$ | Absorb. |
|---|---|
| 12331 | 3.64 |
| 12327 | 3.59 |
| 12323 | 3.54 |
| 12320 | 3.57 |
| 12316 | 3.68 |
| 12312 | 3.68 |
| 12308 | 3.57 |
| 12304 | 3.5 |
| 12300 | 3.48 |
| 12296 | 3.5 |
| 12293 | 3.6 |
| 12289 | 3.66 |
| 12285 | 3.64 |
| 12281 | 3.69 |
| 12277 | 3.7 |
| 12273 | 3.62 |
| 12269 | 3.56 |
| 12266 | 3.53 |
| 12262 | 3.56 |
| 12258 | 3.63 |
| 12254 | 3.74 |
| 12250 | 3.88 |
| 12246 | 3.79 |
| 12242 | 3.7 |
| 12239 | 3.64 |
| 12235 | 3.55 |
| 12231 | 3.48 |
| 12227 | 3.47 |
| 12223 | 3.46 |
| 12219 | 3.45 |
| 12215 | 3.44 |
| 12212 | 3.42 |
| 12208 | 3.47 |
| 12204 | 3.61 |
| 12200 | 3.73 |
| 12196 | 3.67 |
| 12192 | 3.6 |
| 12188 | 3.6 |
| 12185 | 3.61 |
| 12181 | 3.59 |
| 12177 | 3.61 |
| 12173 | 3.66 |
| 12169 | 3.65 |
| 12165 | 3.62 |
| 12161 | 3.62 |
| 12158 | 3.59 |
| 12154 | 3.55 |
| 12150 | 3.56 |
| 12146 | 3.6 |
| 12142 | 3.59 |
| 12138 | 3.57 |
| 12134 | 3.62 |
| 12131 | 3.7 |
| 12127 | 3.73 |
| 12123 | 3.7 |
| 12119 | 3.62 |
| 12115 | 3.57 |
| 12111 | 3.59 |
| 12107 | 3.64 |
| 12104 | 3.62 |
| 12100 | 3.57 |
| 12096 | 3.55 |
| 12092 | 3.54 |
| 12088 | 3.53 |
| 12084 | 3.52 |
| 12080 | 3.53 |
| 12077 | 3.6 |
| 12073 | 3.72 |
| 12069 | 3.76 |
| 12065 | 3.74 |
| 12061 | 3.72 |
| 12057 | 3.71 |
| 12053 | 3.72 |
| 12050 | 3.77 |
| 12046 | 3.78 |
| 12042 | 3.7 |
| 12038 | 3.62 |
| 12034 | 3.64 |

TABLE 3-continued

| cm$^{-1}$ | Absorb. |
|---|---|
| 12030 | 3.8 |
| 12026 | 3.98 |
| 12023 | 3.98 |
| 12019 | 3.87 |
| 12015 | 3.77 |
| 12011 | 3.7 |
| 12007 | 3.71 |
| 12003 | 3.79 |
| 11999 | 3.89 |
| 11996 | 3.88 |
| 11992 | 3.76 |
| 11988 | 3.66 |
| 11984 | 3.63 |
| 11980 | 3.65 |
| 11976 | 3.7 |
| 11972 | 3.78 |
| 11969 | 3.83 |
| 11965 | 3.78 |
| 11961 | 3.69 |
| 11957 | 3.64 |
| 11953 | 3.64 |
| 11949 | 3.69 |
| 11945 | 3.74 |
| 11942 | 3.73 |
| 11938 | 3.73 |
| 11934 | 3.8 |
| 11930 | 3.87 |
| 11926 | 3.89 |
| 11922 | 3.9 |
| 11918 | 3.95 |
| 11915 | 4.06 |
| 11911 | 4.15 |
| 11907 | 4.06 |
| 11903 | 3.94 |
| 11899 | 3.88 |
| 11895 | 3.9 |
| 11891 | 3.92 |
| 11888 | 3.92 |
| 11884 | 4.02 |
| 11880 | 4.12 |
| 11876 | 4.15 |
| 11872 | 4.16 |
| 11868 | 4.13 |
| 11864 | 4.03 |
| 11861 | 4.03 |
| 11857 | 4.28 |
| 11853 | 4.47 |
| 11849 | 4.29 |
| 11845 | 4.1 |
| 11841 | 4.16 |
| 11837 | 4.25 |
| 11834 | 4 |
| 11830 | 3.96 |
| 11826 | 4.01 |
| 11822 | 4.01 |
| 11818 | 4.01 |
| 11814 | 4.01 |
| 11810 | 4.05 |
| 11807 | 4.12 |
| 11803 | 4.17 |
| 11799 | 4.24 |
| 11795 | 4.37 |
| 11791 | 4.18 |
| 11787 | 4.09 |
| 11783 | 4.3 |
| 11780 | 4.27 |
| 11776 | 4.19 |
| 11772 | 4.12 |
| 11768 | 4.18 |
| 11764 | 4.13 |
| 11760 | 4.04 |
| 11756 | 4.05 |
| 11753 | 4.05 |
| 11749 | 4.15 |
| 11745 | 4.25 |
| 11741 | 4.26 |
| 11737 | 4.15 |
| 11733 | 4.17 |
| 11729 | 4.32 |
| 11726 | 4.35 |
| 11722 | 4.32 |
| 11718 | 4.21 |
| 11714 | 4.03 |
| 11710 | 4.08 |
| 11706 | 4.12 |
| 11702 | 4.02 |
| 11699 | 3.96 |
| 11695 | 4.12 |
| 11691 | 4.32 |
| 11687 | 4.4 |
| 11683 | 4.23 |
| 11679 | 4.22 |
| 11675 | 4.29 |
| 11672 | 4.46 |
| 11668 | 4.58 |
| 11664 | 4.41 |
| 11660 | 4.19 |
| 11656 | 4.11 |
| 11652 | 4.1 |
| 11648 | 4.15 |
| 11645 | 4.27 |
| 11641 | 4.2 |
| 11637 | 4.02 |
| 11633 | 4.08 |
| 11629 | 4.14 |
| 11625 | 4.07 |
| 11621 | 4.05 |
| 11618 | 4.11 |
| 11614 | 4.11 |
| 11610 | 4.11 |
| 11606 | 4.07 |
| 11602 | 4.11 |
| 11598 | 4.21 |
| 11594 | 4.15 |
| 11591 | 4.05 |
| 11587 | 3.99 |
| 11583 | 3.98 |
| 11579 | 4.05 |
| 11575 | 4.15 |
| 11571 | 4.21 |
| 11567 | 4.21 |
| 11564 | 4.4 |
| 11560 | 4.54 |
| 11556 | 4.37 |
| 11552 | 4.18 |
| 11548 | 4.18 |
| 11544 | 4.2 |
| 11540 | 4.16 |
| 11537 | 4.16 |
| 11533 | 4.14 |
| 11529 | 4.09 |
| 11525 | 4.05 |
| 11521 | 3.99 |
| 11517 | 3.94 |
| 11513 | 3.98 |
| 11510 | 4.03 |
| 11506 | 4.03 |
| 11502 | 4.04 |
| 11498 | 4.1 |
| 11494 | 4.21 |
| 11490 | 4.33 |
| 11486 | 4.28 |
| 11483 | 4.42 |
| 11479 | 4.27 |
| 11475 | 4.21 |
| 11471 | 4.1 |
| 11467 | 4.12 |
| 11463 | 4.13 |
| 11459 | 4.07 |
| 11456 | 4.16 |
| 11452 | 4.15 |
| 11448 | 4.07 |
| 11444 | 4.09 |
| 11440 | 4.18 |
| 11436 | 4.28 |
| 11432 | 4.2 |

TABLE 3-continued

| cm$^{-1}$ | Absorb. |
|---|---|
| 11429 | 4.1 |
| 11425 | 4.22 |
| 11421 | 4.38 |
| 11417 | 4.25 |
| 11413 | 4.15 |
| 11409 | 4.05 |
| 11405 | 4.01 |
| 11402 | 4.11 |
| 11398 | 4.2 |
| 11394 | 4.26 |
| 11390 | 4.3 |
| 11386 | 4.11 |
| 11382 | 4.01 |
| 11378 | 4.05 |
| 11375 | 4.04 |
| 11371 | 4.02 |
| 11367 | 3.97 |
| 11363 | 3.93 |
| 11359 | 3.93 |
| 11355 | 3.99 |
| 11351 | 4.09 |
| 11348 | 4.18 |
| 11344 | 4.19 |
| 11340 | 4.16 |
| 11336 | 4.16 |
| 11332 | 4.07 |
| 11328 | 3.96 |
| 11324 | 3.94 |
| 11321 | 3.95 |
| 11317 | 4.01 |
| 11313 | 4.07 |
| 11309 | 4 |
| 11305 | 3.89 |
| 11301 | 3.84 |
| 11297 | 3.88 |
| 11294 | 3.97 |
| 11290 | 4.03 |
| 11286 | 3.99 |
| 11282 | 3.89 |
| 11278 | 3.86 |
| 11274 | 3.87 |
| 11270 | 3.85 |
| 11267 | 3.83 |
| 11263 | 3.85 |
| 11259 | 3.85 |
| 11255 | 3.84 |
| 11251 | 3.82 |
| 11247 | 3.82 |
| 11243 | 3.82 |
| 11240 | 3.81 |
| 11236 | 3.78 |
| 11232 | 3.75 |
| 11228 | 3.75 |
| 11224 | 3.83 |
| 11220 | 3.95 |
| 11216 | 4 |
| 11213 | 3.93 |
| 11209 | 3.82 |
| 11205 | 3.79 |
| 11201 | 3.87 |
| 11197 | 3.95 |
| 11193 | 3.89 |
| 11189 | 3.79 |
| 11186 | 3.72 |
| 11182 | 3.74 |
| 11178 | 3.79 |
| 11174 | 3.81 |
| 11170 | 3.8 |
| 11166 | 3.8 |
| 11162 | 3.78 |
| 11159 | 3.74 |
| 11155 | 3.68 |
| 11151 | 3.63 |
| 11147 | 3.62 |
| 11143 | 3.64 |
| 11139 | 3.66 |
| 11135 | 3.64 |
| 11132 | 3.61 |

TABLE 3-continued

| cm$^{-1}$ | Absorb. |
|---|---|
| 11128 | 3.6 |
| 11124 | 3.64 |
| 11120 | 3.65 |
| 11116 | 3.63 |
| 11112 | 3.6 |
| 11108 | 3.56 |
| 11105 | 3.54 |
| 11101 | 3.53 |
| 11097 | 3.52 |
| 11093 | 3.5 |
| 11089 | 3.5 |
| 11085 | 3.51 |
| 11081 | 3.52 |
| 11078 | 3.54 |
| 11074 | 3.54 |
| 11070 | 3.51 |
| 11066 | 3.5 |
| 11062 | 3.52 |
| 11058 | 3.53 |
| 11054 | 3.53 |
| 11051 | 3.52 |
| 11047 | 3.52 |
| 11043 | 3.51 |
| 11039 | 3.5 |
| 11035 | 3.5 |
| 11031 | 3.52 |
| 11027 | 3.53 |
| 11024 | 3.52 |
| 11020 | 3.53 |
| 11016 | 3.52 |
| 11012 | 3.5 |
| 11008 | 3.49 |
| 11004 | 3.5 |
| 11000 | 3.52 |
| 10997 | 3.54 |
| 10993 | 3.53 |
| 10989 | 3.52 |
| 10985 | 3.51 |
| 10981 | 3.51 |
| 10977 | 3.53 |
| 10973 | 3.55 |
| 10970 | 3.56 |
| 10966 | 3.55 |
| 10962 | 3.53 |
| 10958 | 3.53 |
| 10954 | 3.56 |
| 10950 | 3.6 |
| 10946 | 3.6 |
| 10943 | 3.58 |
| 10939 | 3.57 |
| 10935 | 3.59 |
| 10931 | 3.59 |
| 10927 | 3.59 |
| 10923 | 3.56 |
| 10919 | 3.53 |
| 10916 | 3.51 |
| 10912 | 3.51 |
| 10908 | 3.51 |
| 10904 | 3.52 |
| 10900 | 3.53 |
| 10896 | 3.54 |
| 10892 | 3.57 |
| 10889 | 3.59 |
| 10885 | 3.57 |
| 10881 | 3.56 |
| 10877 | 3.58 |
| 10873 | 3.61 |
| 10869 | 3.62 |
| 10865 | 3.62 |
| 10862 | 3.64 |
| 10858 | 3.64 |
| 10854 | 3.63 |
| 10850 | 3.62 |
| 10846 | 3.64 |
| 10842 | 3.68 |
| 10838 | 3.71 |
| 10835 | 3.7 |
| 10831 | 3.66 |

TABLE 3-continued

| cm$^{-1}$ | Absorb. |
|---|---|
| 10827 | 3.64 |
| 10823 | 3.64 |
| 10819 | 3.65 |
| 10815 | 3.67 |
| 10811 | 3.68 |
| 10808 | 3.66 |
| 10804 | 3.63 |
| 10800 | 3.62 |
| 10796 | 3.62 |
| 10792 | 3.64 |
| 10788 | 3.65 |
| 10784 | 3.65 |
| 10781 | 3.62 |
| 10777 | 3.61 |
| 10773 | 3.62 |
| 10769 | 3.64 |
| 10765 | 3.64 |
| 10761 | 3.67 |
| 10757 | 3.7 |
| 10754 | 3.68 |
| 10750 | 3.61 |
| 10746 | 3.58 |
| 10742 | 3.6 |
| 10738 | 3.62 |
| 10734 | 3.64 |
| 10730 | 3.66 |
| 10727 | 3.68 |
| 10723 | 3.68 |
| 10719 | 3.67 |
| 10715 | 3.66 |
| 10711 | 3.67 |
| 10707 | 3.66 |
| 10703 | 3.65 |
| 10700 | 3.64 |
| 10696 | 3.62 |
| 10692 | 3.6 |
| 10688 | 3.6 |
| 10684 | 3.61 |
| 10680 | 3.64 |
| 10676 | 3.67 |
| 10673 | 3.68 |
| 10669 | 3.68 |
| 10665 | 3.67 |
| 10661 | 3.65 |
| 10657 | 3.64 |
| 10653 | 3.65 |
| 10649 | 3.67 |
| 10646 | 3.69 |
| 10642 | 3.69 |
| 10638 | 3.69 |
| 10634 | 3.68 |
| 10630 | 3.66 |
| 10626 | 3.64 |
| 10622 | 3.66 |
| 10619 | 3.68 |
| 10615 | 3.66 |
| 10611 | 3.62 |
| 10607 | 3.61 |
| 10603 | 3.64 |
| 10599 | 3.7 |
| 10595 | 3.75 |
| 10592 | 3.75 |
| 10588 | 3.72 |
| 10584 | 3.71 |
| 10580 | 3.71 |
| 10576 | 3.71 |
| 10572 | 3.71 |
| 10568 | 3.68 |
| 10565 | 3.64 |
| 10561 | 3.63 |
| 10557 | 3.64 |
| 10553 | 3.65 |
| 10549 | 3.66 |
| 10545 | 3.67 |
| 10541 | 3.69 |
| 10538 | 3.69 |
| 10534 | 3.69 |
| 10530 | 3.7 |
| 10526 | 3.71 |
| 10522 | 3.71 |
| 10518 | 3.7 |
| 10514 | 3.68 |
| 10511 | 3.67 |
| 10507 | 3.68 |
| 10503 | 3.71 |
| 10499 | 3.75 |
| 10495 | 3.75 |
| 10491 | 3.72 |
| 10487 | 3.7 |
| 10484 | 3.72 |
| 10480 | 3.75 |
| 10476 | 3.74 |
| 10472 | 3.71 |
| 10468 | 3.72 |
| 10464 | 3.73 |
| 10460 | 3.72 |
| 10457 | 3.72 |
| 10453 | 3.71 |
| 10449 | 3.7 |
| 10445 | 3.72 |
| 10441 | 3.75 |
| 10437 | 3.76 |
| 10433 | 3.73 |
| 10430 | 3.72 |
| 10426 | 3.7 |
| 10422 | 3.67 |
| 10418 | 3.68 |
| 10414 | 3.7 |
| 10410 | 3.74 |
| 10406 | 3.78 |
| 10403 | 3.77 |
| 10399 | 3.75 |
| 10395 | 3.73 |
| 10391 | 3.74 |
| 10387 | 3.74 |
| 10383 | 3.74 |
| 10379 | 3.72 |
| 10376 | 3.72 |
| 10372 | 3.75 |
| 10368 | 3.76 |
| 10364 | 3.77 |
| 10360 | 3.77 |
| 10356 | 3.76 |
| 10352 | 3.75 |
| 10349 | 3.75 |
| 10345 | 3.77 |
| 10341 | 3.77 |
| 10337 | 3.75 |
| 10333 | 3.72 |
| 10329 | 3.68 |
| 10325 | 3.68 |
| 10322 | 3.72 |
| 10318 | 3.77 |
| 10314 | 3.79 |
| 10310 | 3.75 |
| 10306 | 3.73 |
| 10302 | 3.76 |
| 10298 | 3.79 |
| 10295 | 3.76 |
| 10291 | 3.74 |
| 10287 | 3.76 |
| 10283 | 3.79 |
| 10279 | 3.79 |
| 10275 | 3.78 |
| 10271 | 3.78 |
| 10268 | 3.78 |
| 10264 | 3.77 |
| 10260 | 3.76 |
| 10256 | 3.75 |
| 10252 | 3.74 |
| 10248 | 3.76 |
| 10244 | 3.79 |
| 10241 | 3.81 |
| 10237 | 3.77 |
| 10233 | 3.72 |
| 10229 | 3.7 |

TABLE 3-continued

| cm$^{-1}$ | Absorb. |
|---|---|
| 10225 | 3.73 |
| 10221 | 3.77 |
| 10217 | 3.79 |
| 10214 | 3.76 |
| 10210 | 3.73 |
| 10206 | 3.73 |
| 10202 | 3.76 |
| 10198 | 3.77 |
| 10194 | 3.77 |
| 10190 | 3.78 |
| 10187 | 3.78 |
| 10183 | 3.78 |
| 10179 | 3.76 |
| 10175 | 3.75 |
| 10171 | 3.75 |
| 10167 | 3.78 |
| 10163 | 3.78 |
| 10160 | 3.75 |
| 10156 | 3.72 |
| 10152 | 3.73 |
| 10148 | 3.77 |
| 10144 | 3.8 |
| 10140 | 3.78 |
| 10136 | 3.76 |
| 10133 | 3.75 |
| 10129 | 3.74 |
| 10125 | 3.73 |
| 10121 | 3.71 |
| 10117 | 3.69 |
| 10113 | 3.69 |
| 10109 | 3.72 |
| 10106 | 3.73 |
| 10102 | 3.73 |
| 10098 | 3.74 |
| 10094 | 3.77 |
| 10090 | 3.77 |
| 10086 | 3.73 |
| 10082 | 3.71 |
| 10079 | 3.73 |
| 10075 | 3.75 |
| 10071 | 3.75 |
| 10067 | 3.73 |
| 10063 | 3.7 |
| 10059 | 3.71 |
| 10055 | 3.73 |
| 10052 | 3.76 |
| 10048 | 3.76 |
| 10044 | 3.76 |
| 10040 | 3.77 |
| 10036 | 3.78 |
| 10032 | 3.78 |
| 10028 | 3.78 |
| 10025 | 3.79 |
| 10021 | 3.81 |
| 10017 | 3.82 |
| 10013 | 3.8 |
| 10009 | 3.79 |
| 10005 | 3.82 |
| 10002 | 3.88 |
| 9998 | 3.89 |
| 9994 | 3.86 |
| 9990 | 3.83 |
| 9986 | 3.8 |
| 9982 | 3.77 |
| 9978 | 3.75 |
| 9975 | 3.74 |
| 9971 | 3.75 |
| 9967 | 3.77 |
| 9963 | 3.77 |
| 9959 | 3.76 |
| 9955 | 3.75 |
| 9951 | 3.75 |
| 9948 | 3.76 |
| 9944 | 3.79 |
| 9940 | 3.8 |
| 9936 | 3.8 |
| 9932 | 3.78 |
| 9928 | 3.77 |
| 9924 | 3.78 |
| 9921 | 3.78 |
| 9917 | 3.77 |
| 9913 | 3.78 |
| 9909 | 3.78 |
| 9905 | 3.77 |
| 9901 | 3.77 |
| 9897 | 3.78 |
| 9894 | 3.78 |
| 9890 | 3.76 |
| 9886 | 3.74 |
| 9882 | 3.73 |
| 9878 | 3.74 |
| 9874 | 3.77 |
| 9870 | 3.78 |
| 9867 | 3.76 |
| 9863 | 3.76 |
| 9859 | 3.77 |
| 9855 | 3.77 |
| 9851 | 3.74 |
| 9847 | 3.73 |
| 9843 | 3.74 |
| 9840 | 3.75 |
| 9836 | 3.74 |
| 9832 | 3.72 |
| 9828 | 3.73 |
| 9824 | 3.75 |
| 9820 | 3.75 |
| 9816 | 3.73 |
| 9813 | 3.72 |
| 9809 | 3.73 |
| 9805 | 3.74 |
| 9801 | 3.75 |
| 9797 | 3.75 |
| 9793 | 3.73 |
| 9789 | 3.74 |
| 9786 | 3.75 |
| 9782 | 3.76 |
| 9778 | 3.75 |
| 9774 | 3.73 |
| 9770 | 3.71 |
| 9766 | 3.7 |
| 9762 | 3.7 |
| 9759 | 3.71 |
| 9755 | 3.72 |
| 9751 | 3.72 |
| 9747 | 3.73 |
| 9743 | 3.73 |
| 9739 | 3.73 |
| 9735 | 3.72 |
| 9732 | 3.72 |
| 9728 | 3.7 |
| 9724 | 3.69 |
| 9720 | 3.69 |
| 9716 | 3.7 |
| 9712 | 3.72 |
| 9708 | 3.74 |
| 9705 | 3.74 |
| 9701 | 3.73 |
| 9697 | 3.72 |
| 9693 | 3.72 |
| 9689 | 3.72 |
| 9685 | 3.72 |
| 9681 | 3.72 |
| 9678 | 3.71 |
| 9674 | 3.71 |
| 9670 | 3.72 |
| 9666 | 3.72 |
| 9662 | 3.71 |
| 9658 | 3.7 |
| 9654 | 3.7 |
| 9651 | 3.71 |
| 9647 | 3.71 |
| 9643 | 3.69 |
| 9639 | 3.67 |
| 9635 | 3.67 |
| 9631 | 3.7 |
| 9627 | 3.73 |

TABLE 3-continued

| cm⁻¹ | Absorb. |
|---|---|
| 9624 | 3.72 |
| 9620 | 3.7 |
| 9616 | 3.68 |
| 9612 | 3.68 |
| 9608 | 3.68 |
| 9604 | 3.7 |
| 9600 | 3.72 |
| 9597 | 3.72 |
| 9593 | 3.71 |
| 9589 | 3.7 |
| 9585 | 3.71 |
| 9581 | 3.71 |
| 9577 | 3.7 |
| 9573 | 3.7 |
| 9570 | 3.72 |
| 9566 | 3.74 |
| 9562 | 3.72 |
| 9558 | 3.71 |
| 9554 | 3.72 |
| 9550 | 3.74 |
| 9546 | 3.74 |
| 9543 | 3.74 |
| 9539 | 3.74 |
| 9535 | 3.74 |
| 9531 | 3.76 |
| 9527 | 3.77 |
| 9523 | 3.77 |
| 9519 | 3.77 |
| 9516 | 3.73 |
| 9512 | 3.71 |
| 9508 | 3.71 |
| 9504 | 3.73 |
| 9500 | 3.76 |
| 9496 | 3.78 |
| 9492 | 3.78 |
| 9489 | 3.77 |
| 9485 | 3.75 |
| 9481 | 3.73 |
| 9477 | 3.73 |
| 9473 | 3.75 |
| 9469 | 3.77 |
| 9465 | 3.77 |
| 9462 | 3.76 |
| 9458 | 3.76 |
| 9454 | 3.76 |
| 9450 | 3.76 |
| 9446 | 3.77 |
| 9442 | 3.78 |
| 9438 | 3.78 |
| 9435 | 3.77 |
| 9431 | 3.76 |
| 9427 | 3.76 |
| 9423 | 3.77 |
| 9419 | 3.78 |
| 9415 | 3.78 |
| 9411 | 3.8 |
| 9408 | 3.81 |
| 9404 | 3.82 |
| 9400 | 3.83 |
| 9396 | 3.84 |
| 9392 | 3.83 |
| 9388 | 3.83 |
| 9384 | 3.84 |
| 9381 | 3.86 |
| 9377 | 3.87 |
| 9373 | 3.88 |
| 9369 | 3.89 |
| 9365 | 3.91 |
| 9361 | 3.92 |
| 9357 | 3.91 |
| 9354 | 3.9 |
| 9350 | 3.89 |
| 9346 | 3.91 |
| 9342 | 3.94 |
| 9338 | 3.99 |
| 9334 | 4.02 |
| 9330 | 4.02 |
| 9327 | 4.01 |
| 9323 | 4.01 |
| 9319 | 4.04 |
| 9315 | 4.06 |
| 9311 | 4.05 |
| 9307 | 4.06 |
| 9303 | 4.09 |
| 9300 | 4.1 |
| 9296 | 4.1 |
| 9292 | 4.11 |
| 9288 | 4.11 |
| 9284 | 4.11 |
| 9280 | 4.1 |
| 9276 | 4.1 |
| 9273 | 4.14 |
| 9269 | 4.18 |
| 9265 | 4.17 |
| 9261 | 4.17 |
| 9257 | 4.17 |
| 9253 | 4.17 |
| 9249 | 4.18 |
| 9246 | 4.2 |
| 9242 | 4.19 |
| 9238 | 4.19 |
| 9234 | 4.24 |
| 9230 | 4.38 |
| 9226 | 4.44 |
| 9222 | 4.3 |
| 9219 | 4.2 |
| 9215 | 4.21 |
| 9211 | 4.27 |
| 9207 | 4.33 |
| 9203 | 4.37 |
| 9199 | 4.35 |
| 9195 | 4.31 |
| 9192 | 4.3 |
| 9188 | 4.29 |
| 9184 | 4.3 |
| 9180 | 4.32 |
| 9176 | 4.32 |
| 9172 | 4.28 |
| 9168 | 4.22 |
| 9165 | 4.17 |
| 9161 | 4.16 |
| 9157 | 4.19 |
| 9153 | 4.23 |
| 9149 | 4.27 |
| 9145 | 4.34 |
| 9141 | 4.41 |
| 9138 | 4.43 |
| 9134 | 4.4 |
| 9130 | 4.39 |
| 9126 | 4.37 |
| 9122 | 4.29 |
| 9118 | 4.27 |
| 9114 | 4.31 |
| 9111 | 4.34 |
| 9107 | 4.34 |
| 9103 | 4.37 |
| 9099 | 4.43 |
| 9095 | 4.44 |
| 9091 | 4.37 |
| 9087 | 4.28 |
| 9084 | 4.25 |
| 9080 | 4.3 |
| 9076 | 4.42 |
| 9072 | 4.48 |
| 9068 | 4.41 |
| 9064 | 4.36 |
| 9060 | 4.36 |
| 9057 | 4.37 |
| 9053 | 4.35 |
| 9049 | 4.36 |
| 9045 | 4.38 |
| 9041 | 4.45 |
| 9037 | 4.52 |
| 9033 | 4.51 |
| 9030 | 4.42 |
| 9026 | 4.34 |

TABLE 3-continued

| cm⁻¹ | Absorb. |
|---|---|
| 9022 | 4.32 |
| 9018 | 4.34 |
| 9014 | 4.37 |
| 9010 | 4.41 |
| 9006 | 4.45 |
| 9003 | 4.44 |
| 8999 | 4.43 |
| 8995 | 4.49 |
| 8991 | 4.55 |
| 8987 | 4.57 |
| 8983 | 4.57 |
| 8979 | 4.58 |
| 8976 | 4.58 |
| 8972 | 4.55 |
| 8968 | 4.48 |
| 8964 | 4.46 |
| 8960 | 4.49 |
| 8956 | 4.52 |
| 8952 | 4.53 |
| 8949 | 4.55 |
| 8945 | 4.59 |
| 8941 | 4.62 |
| 8937 | 4.65 |
| 8933 | 4.69 |
| 8929 | 4.73 |
| 8925 | 4.77 |
| 8922 | 4.86 |
| 8918 | 4.84 |
| 8914 | 4.75 |
| 8910 | 4.82 |
| 8906 | 4.98 |
| 8902 | 5.07 |
| 8898 | 4.85 |
| 8895 | 4.72 |
| 8891 | 4.68 |
| 8887 | 4.79 |
| 8883 | 5.05 |
| 8879 | 4.87 |
| 8875 | 4.98 |
| 8871 | 5.11 |
| 8868 | 5.22 |
| 8864 | 5.1 |
| 8860 | 4.98 |
| 8856 | 4.93 |
| 8852 | 4.99 |
| 8848 | 5.02 |
| 8844 | 4.72 |
| 8841 | 4.65 |
| 8837 | 4.74 |
| 8833 | 4.88 |
| 8829 | 4.92 |
| 8825 | 4.94 |
| 8821 | 4.85 |
| 8817 | 4.73 |
| 8814 | 4.81 |
| 8810 | 5.14 |
| 8806 | 5.04 |
| 8802 | 4.98 |
| 8798 | 4.94 |
| 8794 | 5.18 |
| 8790 | 5.24 |
| 8787 | 5.23 |
| 8783 | 5.04 |
| 8779 | 4.91 |
| 8775 | 4.95 |
| 8771 | 5.01 |
| 8767 | 4.97 |
| 8763 | 4.89 |
| 8760 | 4.83 |
| 8756 | 4.84 |
| 8752 | 4.89 |
| 8748 | 4.8 |
| 8744 | 4.82 |
| 8740 | 5.06 |
| 8736 | 5.1 |
| 8733 | 4.99 |
| 8729 | 4.98 |
| 8725 | 4.95 |
| 8721 | 4.87 |
| 8717 | 4.93 |
| 8713 | 4.93 |
| 8709 | 4.84 |
| 8706 | 5.04 |
| 8702 | 5.14 |
| 8698 | 5.07 |
| 8694 | 5.2 |
| 8690 | 5.17 |
| 8686 | 5.13 |
| 8682 | 5.54 |
| 8679 | 5.32 |
| 8675 | 5.11 |
| 8671 | 5.29 |
| 8667 | 5.02 |
| 8663 | 4.72 |
| 8659 | 4.72 |
| 8655 | 4.85 |
| 8652 | 4.95 |
| 8648 | 4.98 |
| 8644 | 4.99 |
| 8640 | 4.99 |
| 8636 | 4.97 |
| 8632 | 4.96 |
| 8628 | 4.93 |
| 8625 | 4.88 |
| 8621 | 4.98 |
| 8617 | 5.51 |
| 8613 | 5.23 |
| 8609 | 5.12 |
| 8605 | 5.18 |
| 8601 | 5.05 |
| 8598 | 4.87 |
| 8594 | 4.85 |
| 8590 | 4.85 |
| 8586 | 5.01 |
| 8582 | 5.73 |
| 8578 | 4.99 |
| 8574 | 4.93 |
| 8571 | 4.96 |
| 8567 | 4.96 |
| 8563 | 5.04 |
| 8559 | 5.13 |
| 8555 | 5.1 |
| 8551 | 4.93 |
| 8547 | 4.8 |
| 8544 | 4.75 |
| 8540 | 4.76 |
| 8536 | 4.87 |
| 8532 | 5 |
| 8528 | 4.92 |
| 8524 | 4.93 |
| 8520 | 5.1 |
| 8517 | 5.32 |
| 8513 | 5.09 |
| 8509 | 4.82 |
| 8505 | 4.77 |
| 8501 | 4.84 |
| 8497 | 4.93 |
| 8493 | 4.81 |
| 8490 | 4.71 |
| 8486 | 4.74 |
| 8482 | 4.77 |
| 8478 | 4.77 |
| 8474 | 4.96 |
| 8470 | 5.11 |
| 8466 | 5.21 |
| 8463 | 5.07 |
| 8459 | 5.16 |
| 8455 | 5.11 |
| 8451 | 4.99 |
| 8447 | 4.92 |
| 8443 | 4.86 |
| 8439 | 4.93 |
| 8436 | 5.09 |
| 8432 | 5.09 |
| 8428 | 4.88 |
| 8424 | 4.85 |

TABLE 3-continued

| cm$^{-1}$ | Absorb. |
|---|---|
| 8420 | 4.85 |
| 8416 | 4.85 |
| 8412 | 4.89 |
| 8409 | 5.09 |
| 8405 | 5.13 |
| 8401 | 5.06 |
| 8397 | 5.13 |
| 8393 | 5.04 |
| 8389 | 4.97 |
| 8385 | 5.11 |
| 8382 | 5.1 |
| 8378 | 5.06 |
| 8374 | 5.15 |
| 8370 | 5.08 |
| 8366 | 4.98 |
| 8362 | 4.88 |
| 8358 | 4.8 |
| 8355 | 4.81 |
| 8351 | 4.97 |
| 8347 | 5.11 |
| 8343 | 5.15 |
| 8339 | 5.36 |
| 8335 | 5.12 |
| 8331 | 5.03 |
| 8328 | 5.05 |
| 8324 | 5.1 |
| 8320 | 5.05 |
| 8316 | 5.14 |
| 8312 | 5.12 |
| 8308 | 5.05 |
| 8304 | 5.2 |
| 8301 | 4.99 |
| 8297 | 4.94 |
| 8293 | 5.27 |
| 8289 | 5.18 |
| 8285 | 5.06 |
| 8281 | 5.11 |
| 8277 | 5.06 |
| 8274 | 4.98 |
| 8270 | 4.96 |
| 8266 | 4.97 |
| 8262 | 4.99 |
| 8258 | 5.01 |
| 8254 | 5.07 |
| 8250 | 5.24 |
| 8247 | 5.24 |
| 8243 | 5.14 |
| 8239 | 5.21 |
| 8235 | 4.98 |
| 8231 | 4.82 |
| 8227 | 4.8 |
| 8223 | 4.8 |
| 8220 | 4.73 |
| 8216 | 4.69 |
| 8212 | 4.8 |
| 8208 | 4.87 |
| 8204 | 4.87 |
| 8200 | 4.84 |
| 8196 | 4.78 |
| 8193 | 4.75 |
| 8189 | 4.77 |
| 8185 | 4.84 |
| 8181 | 4.83 |
| 8177 | 4.67 |
| 8173 | 4.57 |
| 8169 | 4.56 |
| 8166 | 4.65 |
| 8162 | 4.74 |
| 8158 | 4.73 |
| 8154 | 4.73 |
| 8150 | 4.77 |
| 8146 | 4.82 |
| 8142 | 4.84 |
| 8139 | 4.79 |
| 8135 | 4.68 |
| 8131 | 4.57 |
| 8127 | 4.54 |
| 8123 | 4.55 |

TABLE 3-continued

| cm$^{-1}$ | Absorb. |
|---|---|
| 8119 | 4.56 |
| 8115 | 4.59 |
| 8112 | 4.58 |
| 8108 | 4.57 |
| 8104 | 4.57 |
| 8100 | 4.54 |
| 8096 | 4.49 |
| 8092 | 4.45 |
| 8088 | 4.43 |
| 8085 | 4.44 |
| 8081 | 4.44 |
| 8077 | 4.46 |
| 8073 | 4.45 |
| 8069 | 4.39 |
| 8065 | 4.35 |
| 8061 | 4.35 |
| 8058 | 4.37 |
| 8054 | 4.4 |
| 8050 | 4.44 |
| 8046 | 4.44 |
| 8042 | 4.38 |
| 8038 | 4.36 |
| 8034 | 4.39 |
| 8031 | 4.38 |
| 8027 | 4.35 |
| 8023 | 4.33 |
| 8019 | 4.3 |
| 8015 | 4.26 |
| 8011 | 4.25 |
| 8007 | 4.27 |
| 8004 | 4.29 |
| 8000 | 4.27 |
| 7996 | 4.25 |
| 7992 | 4.23 |
| 7988 | 4.25 |
| 7984 | 4.26 |
| 7980 | 4.26 |
| 7977 | 4.24 |
| 7973 | 4.2 |
| 7969 | 4.18 |
| 7965 | 4.18 |
| 7961 | 4.19 |
| 7957 | 4.19 |
| 7953 | 4.17 |
| 7950 | 4.15 |
| 7946 | 4.15 |
| 7942 | 4.16 |
| 7938 | 4.18 |
| 7934 | 4.18 |
| 7930 | 4.16 |
| 7926 | 4.13 |
| 7923 | 4.1 |
| 7919 | 4.07 |
| 7915 | 4.07 |
| 7911 | 4.09 |
| 7907 | 4.09 |
| 7903 | 4.07 |
| 7899 | 4.05 |
| 7896 | 4.05 |
| 7892 | 4.06 |
| 7888 | 4.05 |
| 7884 | 4.03 |
| 7880 | 4.02 |
| 7876 | 4.01 |
| 7872 | 3.99 |
| 7869 | 3.97 |
| 7865 | 3.97 |
| 7861 | 3.97 |
| 7857 | 3.96 |
| 7853 | 3.96 |
| 7849 | 3.96 |
| 7845 | 3.96 |
| 7842 | 3.95 |
| 7838 | 3.95 |
| 7834 | 3.94 |
| 7830 | 3.92 |
| 7826 | 3.91 |
| 7822 | 3.91 |

TABLE 3-continued

| cm$^{-1}$ | Absorb. |
|---|---|
| 7818 | 3.9 |
| 7815 | 3.9 |
| 7811 | 3.89 |
| 7807 | 3.88 |
| 7803 | 3.88 |
| 7799 | 3.88 |
| 7795 | 3.88 |
| 7791 | 3.88 |
| 7788 | 3.87 |
| 7784 | 3.86 |
| 7780 | 3.84 |
| 7776 | 3.84 |
| 7772 | 3.83 |
| 7768 | 3.82 |
| 7764 | 3.81 |
| 7761 | 3.8 |
| 7757 | 3.79 |
| 7753 | 3.79 |
| 7749 | 3.79 |
| 7745 | 3.78 |
| 7741 | 3.78 |
| 7737 | 3.78 |
| 7734 | 3.77 |
| 7730 | 3.76 |
| 7726 | 3.75 |
| 7722 | 3.74 |
| 7718 | 3.73 |
| 7714 | 3.72 |
| 7710 | 3.72 |
| 7707 | 3.72 |
| 7703 | 3.7 |
| 7699 | 3.68 |
| 7695 | 3.66 |
| 7691 | 3.65 |
| 7687 | 3.65 |
| 7683 | 3.65 |
| 7680 | 3.65 |
| 7676 | 3.64 |
| 7672 | 3.63 |
| 7668 | 3.63 |
| 7664 | 3.63 |
| 7660 | 3.62 |
| 7656 | 3.61 |
| 7653 | 3.6 |
| 7649 | 3.6 |
| 7645 | 3.59 |
| 7641 | 3.59 |
| 7637 | 3.57 |
| 7633 | 3.56 |
| 7629 | 3.56 |
| 7626 | 3.55 |
| 7622 | 3.54 |
| 7618 | 3.54 |
| 7614 | 3.53 |
| 7610 | 3.53 |
| 7606 | 3.53 |
| 7602 | 3.52 |
| 7599 | 3.51 |
| 7595 | 3.5 |
| 7591 | 3.5 |
| 7587 | 3.49 |
| 7583 | 3.48 |
| 7579 | 3.48 |
| 7575 | 3.48 |
| 7572 | 3.47 |
| 7568 | 3.46 |
| 7564 | 3.46 |
| 7560 | 3.45 |
| 7556 | 3.44 |
| 7552 | 3.44 |
| 7548 | 3.43 |
| 7545 | 3.42 |
| 7541 | 3.41 |
| 7537 | 3.41 |
| 7533 | 3.4 |
| 7529 | 3.4 |
| 7525 | 3.4 |
| 7521 | 3.39 |
| 7518 | 3.38 |
| 7514 | 3.37 |
| 7510 | 3.36 |
| 7506 | 3.36 |
| 7502 | 3.35 |
| 7498 | 3.35 |
| 7494 | 3.34 |
| 7491 | 3.33 |
| 7487 | 3.33 |
| 7483 | 3.32 |
| 7479 | 3.32 |
| 7475 | 3.31 |
| 7471 | 3.31 |
| 7467 | 3.3 |
| 7464 | 3.29 |
| 7460 | 3.29 |
| 7456 | 3.28 |
| 7452 | 3.28 |
| 7448 | 3.27 |
| 7444 | 3.27 |
| 7440 | 3.26 |
| 7437 | 3.26 |
| 7433 | 3.25 |
| 7429 | 3.25 |
| 7425 | 3.24 |
| 7421 | 3.24 |
| 7417 | 3.23 |
| 7413 | 3.23 |
| 7410 | 3.22 |
| 7406 | 3.22 |
| 7402 | 3.21 |
| 7398 | 3.21 |
| 7394 | 3.21 |
| 7390 | 3.21 |
| 7386 | 3.21 |
| 7383 | 3.21 |
| 7379 | 3.21 |
| 7375 | 3.2 |
| 7371 | 3.2 |
| 7367 | 3.2 |
| 7363 | 3.2 |
| 7359 | 3.21 |
| 7356 | 3.21 |
| 7352 | 3.21 |
| 7348 | 3.21 |
| 7344 | 3.21 |
| 7340 | 3.2 |
| 7336 | 3.2 |
| 7332 | 3.19 |
| 7329 | 3.19 |
| 7325 | 3.18 |
| 7321 | 3.18 |
| 7317 | 3.18 |
| 7313 | 3.18 |
| 7309 | 3.18 |
| 7305 | 3.17 |
| 7302 | 3.17 |
| 7298 | 3.17 |
| 7294 | 3.17 |
| 7290 | 3.17 |
| 7286 | 3.18 |
| 7282 | 3.18 |
| 7278 | 3.18 |
| 7275 | 3.18 |
| 7271 | 3.18 |
| 7267 | 3.18 |
| 7263 | 3.18 |
| 7259 | 3.19 |
| 7255 | 3.19 |
| 7251 | 3.19 |
| 7248 | 3.19 |
| 7244 | 3.19 |
| 7240 | 3.19 |
| 7236 | 3.19 |
| 7232 | 3.19 |
| 7228 | 3.19 |
| 7224 | 3.19 |
| 7221 | 3.19 |

TABLE 3-continued

| cm⁻¹ | Absorb. |
|---|---|
| 7217 | 3.19 |
| 7213 | 3.19 |
| 7209 | 3.2 |
| 7205 | 3.2 |
| 7201 | 3.2 |
| 7197 | 3.2 |
| 7194 | 3.2 |
| 7190 | 3.21 |
| 7186 | 3.21 |
| 7182 | 3.2 |
| 7178 | 3.19 |
| 7174 | 3.18 |
| 7170 | 3.17 |
| 7167 | 3.16 |
| 7163 | 3.14 |
| 7159 | 3.12 |
| 7155 | 3.11 |
| 7151 | 3.1 |
| 7147 | 3.08 |
| 7143 | 3.07 |
| 7140 | 3.06 |
| 7136 | 3.05 |
| 7132 | 3.04 |
| 7128 | 3.04 |
| 7124 | 3.03 |
| 7120 | 3.03 |
| 7116 | 3.02 |
| 7113 | 3.02 |
| 7109 | 3.02 |
| 7105 | 3.02 |
| 7101 | 3.02 |
| 7097 | 3.02 |
| 7093 | 3.02 |
| 7089 | 3.02 |
| 7086 | 3.02 |
| 7082 | 3.02 |
| 7078 | 3.02 |
| 7074 | 3.01 |
| 7070 | 3 |
| 7066 | 2.99 |
| 7062 | 2.97 |
| 7059 | 2.96 |
| 7055 | 2.95 |
| 7051 | 2.93 |
| 7047 | 2.92 |
| 7043 | 2.91 |
| 7039 | 2.9 |
| 7035 | 2.89 |
| 7032 | 2.88 |
| 7028 | 2.88 |
| 7024 | 2.87 |
| 7020 | 2.86 |
| 7016 | 2.86 |
| 7012 | 2.85 |
| 7008 | 2.84 |
| 7005 | 2.84 |
| 7001 | 2.83 |
| 6997 | 2.83 |
| 6993 | 2.83 |
| 6989 | 2.82 |
| 6985 | 2.82 |
| 6981 | 2.81 |
| 6978 | 2.81 |
| 6974 | 2.8 |
| 6970 | 2.79 |
| 6966 | 2.78 |
| 6962 | 2.78 |
| 6958 | 2.77 |
| 6954 | 2.76 |
| 6951 | 2.75 |
| 6947 | 2.74 |
| 6943 | 2.74 |
| 6939 | 2.73 |
| 6935 | 2.72 |
| 6931 | 2.71 |
| 6927 | 2.7 |
| 6924 | 2.7 |
| 6920 | 2.69 |

TABLE 3-continued

| cm⁻¹ | Absorb. |
|---|---|
| 6916 | 2.68 |
| 6912 | 2.67 |
| 6908 | 2.67 |
| 6904 | 2.66 |
| 6900 | 2.65 |
| 6897 | 2.64 |
| 6893 | 2.63 |
| 6889 | 2.63 |
| 6885 | 2.62 |
| 6881 | 2.61 |
| 6877 | 2.6 |
| 6873 | 2.59 |
| 6870 | 2.59 |
| 6866 | 2.58 |
| 6862 | 2.57 |
| 6858 | 2.57 |
| 6854 | 2.56 |
| 6850 | 2.56 |
| 6846 | 2.55 |
| 6843 | 2.54 |
| 6839 | 2.54 |
| 6835 | 2.53 |
| 6831 | 2.53 |
| 6827 | 2.52 |
| 6823 | 2.52 |
| 6819 | 2.51 |
| 6816 | 2.51 |
| 6812 | 2.5 |
| 6808 | 2.49 |
| 6804 | 2.49 |
| 6800 | 2.48 |
| 6796 | 2.48 |
| 6792 | 2.47 |
| 6789 | 2.46 |
| 6785 | 2.45 |
| 6781 | 2.45 |
| 6777 | 2.44 |
| 6773 | 2.44 |
| 6769 | 2.43 |
| 6765 | 2.42 |
| 6762 | 2.42 |
| 6758 | 2.41 |
| 6754 | 2.41 |
| 6750 | 2.4 |
| 6746 | 2.39 |
| 6742 | 2.39 |
| 6738 | 2.38 |
| 6735 | 2.38 |
| 6731 | 2.37 |
| 6727 | 2.37 |
| 6723 | 2.36 |
| 6719 | 2.36 |
| 6715 | 2.35 |
| 6711 | 2.34 |
| 6708 | 2.34 |
| 6704 | 2.33 |
| 6700 | 2.33 |
| 6696 | 2.32 |
| 6692 | 2.32 |
| 6688 | 2.31 |
| 6684 | 2.31 |
| 6681 | 2.3 |
| 6677 | 2.3 |
| 6673 | 2.29 |
| 6669 | 2.28 |
| 6665 | 2.28 |
| 6661 | 2.27 |
| 6657 | 2.27 |
| 6654 | 2.26 |
| 6650 | 2.26 |
| 6646 | 2.25 |
| 6642 | 2.25 |
| 6638 | 2.24 |
| 6634 | 2.23 |
| 6630 | 2.23 |
| 6627 | 2.22 |
| 6623 | 2.22 |
| 6619 | 2.21 |

TABLE 3-continued

| cm⁻¹ | Absorb. |
|---|---|
| 6615 | 2.21 |
| 6611 | 2.2 |
| 6607 | 2.2 |
| 6603 | 2.19 |
| 6600 | 2.19 |
| 6596 | 2.18 |
| 6592 | 2.18 |
| 6588 | 2.17 |
| 6584 | 2.17 |
| 6580 | 2.16 |
| 6576 | 2.16 |
| 6573 | 2.15 |
| 6569 | 2.15 |
| 6565 | 2.15 |
| 6561 | 2.14 |
| 6557 | 2.14 |
| 6553 | 2.13 |
| 6549 | 2.13 |
| 6546 | 2.12 |
| 6542 | 2.12 |
| 6538 | 2.11 |
| 6534 | 2.11 |
| 6530 | 2.11 |
| 6526 | 2.1 |
| 6522 | 2.1 |
| 6519 | 2.09 |
| 6515 | 2.09 |
| 6511 | 2.08 |
| 6507 | 2.08 |
| 6503 | 2.07 |
| 6499 | 2.07 |
| 6495 | 2.07 |
| 6492 | 2.06 |
| 6488 | 2.06 |
| 6484 | 2.05 |
| 6480 | 2.05 |
| 6476 | 2.04 |
| 6472 | 2.04 |
| 6468 | 2.03 |
| 6465 | 2.03 |
| 6461 | 2.02 |
| 6457 | 2.02 |
| 6453 | 2.01 |
| 6449 | 2.01 |
| 6445 | 2 |
| 6441 | 2 |
| 6438 | 2 |
| 6434 | 1.99 |
| 6430 | 1.99 |
| 6426 | 1.98 |
| 6422 | 1.98 |
| 6418 | 1.97 |
| 6414 | 1.97 |
| 6411 | 1.97 |
| 6407 | 1.96 |
| 6403 | 1.96 |
| 6399 | 1.96 |
| 6395 | 1.95 |
| 6391 | 1.95 |
| 6387 | 1.94 |
| 6384 | 1.94 |
| 6380 | 1.94 |
| 6376 | 1.93 |
| 6372 | 1.93 |
| 6368 | 1.92 |
| 6364 | 1.92 |
| 6360 | 1.92 |
| 6357 | 1.91 |
| 6353 | 1.91 |
| 6349 | 1.91 |
| 6345 | 1.9 |
| 6341 | 1.9 |
| 6337 | 1.9 |
| 6333 | 1.89 |
| 6330 | 1.89 |
| 6326 | 1.89 |
| 6322 | 1.88 |
| 6318 | 1.88 |
| 6314 | 1.88 |
| 6310 | 1.87 |
| 6306 | 1.87 |
| 6303 | 1.87 |
| 6299 | 1.86 |
| 6295 | 1.86 |
| 6291 | 1.86 |
| 6287 | 1.85 |
| 6283 | 1.85 |
| 6279 | 1.85 |
| 6276 | 1.84 |
| 6272 | 1.84 |
| 6268 | 1.84 |
| 6264 | 1.84 |
| 6260 | 1.83 |
| 6256 | 1.83 |
| 6252 | 1.83 |
| 6249 | 1.82 |
| 6245 | 1.82 |
| 6241 | 1.82 |
| 6237 | 1.82 |
| 6233 | 1.81 |
| 6229 | 1.81 |
| 6225 | 1.81 |
| 6222 | 1.81 |
| 6218 | 1.8 |
| 6214 | 1.8 |
| 6210 | 1.8 |
| 6206 | 1.8 |
| 6202 | 1.79 |
| 6198 | 1.79 |
| 6195 | 1.79 |
| 6191 | 1.79 |
| 6187 | 1.79 |
| 6183 | 1.79 |
| 6179 | 1.79 |
| 6175 | 1.78 |
| 6171 | 1.78 |
| 6168 | 1.78 |
| 6164 | 1.78 |
| 6160 | 1.78 |
| 6156 | 1.78 |
| 6152 | 1.78 |
| 6148 | 1.78 |
| 6144 | 1.79 |
| 6141 | 1.79 |
| 6137 | 1.79 |
| 6133 | 1.79 |
| 6129 | 1.79 |
| 6125 | 1.79 |
| 6121 | 1.79 |
| 6117 | 1.79 |
| 6114 | 1.79 |
| 6110 | 1.79 |
| 6106 | 1.79 |
| 6102 | 1.79 |
| 6098 | 1.79 |
| 6094 | 1.79 |
| 6090 | 1.79 |
| 6087 | 1.79 |
| 6083 | 1.79 |
| 6079 | 1.79 |
| 6075 | 1.79 |
| 6071 | 1.78 |
| 6067 | 1.78 |
| 6063 | 1.78 |
| 6060 | 1.78 |
| 6056 | 1.79 |
| 6052 | 1.79 |
| 6048 | 1.79 |
| 6044 | 1.79 |
| 6040 | 1.8 |
| 6036 | 1.8 |
| 6033 | 1.81 |
| 6029 | 1.82 |
| 6025 | 1.82 |
| 6021 | 1.83 |
| 6017 | 1.84 |

TABLE 3-continued

| cm$^{-1}$ | Absorb. |
|---|---|
| 6013 | 1.86 |
| 6009 | 1.87 |
| 6006 | 1.88 |
| 6002 | 1.89 |
| 5998 | 1.91 |
| 5994 | 1.93 |
| 5990 | 1.94 |
| 5986 | 1.96 |
| 5982 | 1.98 |
| 5979 | 2 |
| 5975 | 2.02 |
| 5971 | 2.04 |
| 5967 | 2.07 |
| 5963 | 2.09 |
| 5959 | 2.11 |
| 5955 | 2.14 |
| 5952 | 2.17 |
| 5948 | 2.2 |
| 5944 | 2.24 |
| 5940 | 2.28 |
| 5936 | 2.34 |
| 5932 | 2.4 |
| 5928 | 2.48 |
| 5925 | 2.58 |
| 5921 | 2.68 |
| 5917 | 2.79 |
| 5913 | 2.89 |
| 5909 | 2.98 |
| 5905 | 3.03 |
| 5901 | 3.06 |
| 5898 | 3.07 |
| 5894 | 3.09 |
| 5890 | 3.12 |
| 5886 | 3.17 |
| 5882 | 3.25 |
| 5878 | 3.34 |
| 5874 | 3.44 |
| 5871 | 3.52 |
| 5867 | 3.57 |
| 5863 | 3.58 |
| 5859 | 3.57 |
| 5855 | 3.55 |
| 5851 | 3.53 |
| 5847 | 3.52 |
| 5844 | 3.53 |
| 5840 | 3.54 |
| 5836 | 3.58 |
| 5832 | 3.63 |
| 5828 | 3.69 |
| 5824 | 3.75 |
| 5820 | 3.82 |
| 5817 | 3.89 |
| 5813 | 3.96 |
| 5809 | 4.02 |
| 5805 | 4.07 |
| 5801 | 4.1 |
| 5797 | 4.11 |
| 5793 | 4.09 |
| 5790 | 4.07 |
| 5786 | 4.04 |
| 5782 | 3.99 |
| 5778 | 3.93 |
| 5774 | 3.86 |
| 5770 | 3.76 |
| 5766 | 3.66 |
| 5763 | 3.55 |
| 5759 | 3.46 |
| 5755 | 3.37 |
| 5751 | 3.28 |
| 5747 | 3.21 |
| 5743 | 3.14 |
| 5739 | 3.09 |
| 5736 | 3.05 |
| 5732 | 3.03 |
| 5728 | 3.02 |
| 5724 | 3.02 |
| 5720 | 3.03 |
| 5716 | 3.04 |

TABLE 3-continued

| cm$^{-1}$ | Absorb. |
|---|---|
| 5712 | 3.05 |
| 5709 | 3.06 |
| 5705 | 3.08 |
| 5701 | 3.1 |
| 5697 | 3.12 |
| 5693 | 3.15 |
| 5689 | 3.18 |
| 5685 | 3.2 |
| 5682 | 3.23 |
| 5678 | 3.24 |
| 5674 | 3.24 |
| 5670 | 3.23 |
| 5666 | 3.19 |
| 5662 | 3.15 |
| 5658 | 3.09 |
| 5655 | 3.03 |
| 5651 | 2.96 |
| 5647 | 2.9 |
| 5643 | 2.84 |
| 5639 | 2.78 |
| 5635 | 2.72 |
| 5631 | 2.66 |
| 5628 | 2.6 |
| 5624 | 2.54 |
| 5620 | 2.49 |
| 5616 | 2.44 |
| 5612 | 2.39 |
| 5608 | 2.35 |
| 5604 | 2.31 |
| 5601 | 2.28 |
| 5597 | 2.26 |
| 5593 | 2.24 |
| 5589 | 2.22 |
| 5585 | 2.21 |
| 5581 | 2.2 |
| 5577 | 2.2 |
| 5574 | 2.19 |
| 5570 | 2.18 |
| 5566 | 2.18 |
| 5562 | 2.17 |
| 5558 | 2.17 |
| 5554 | 2.16 |
| 5550 | 2.15 |
| 5547 | 2.15 |
| 5543 | 2.14 |
| 5539 | 2.13 |
| 5535 | 2.13 |
| 5531 | 2.12 |
| 5527 | 2.12 |
| 5523 | 2.12 |
| 5520 | 2.12 |
| 5516 | 2.12 |
| 5512 | 2.12 |
| 5508 | 2.12 |
| 5504 | 2.12 |
| 5500 | 2.12 |
| 5496 | 2.12 |
| 5493 | 2.11 |
| 5489 | 2.11 |
| 5485 | 2.1 |
| 5481 | 2.1 |
| 5477 | 2.09 |
| 5473 | 2.08 |
| 5469 | 2.08 |
| 5466 | 2.07 |
| 5462 | 2.06 |
| 5458 | 2.04 |
| 5454 | 2.03 |
| 5450 | 2.02 |
| 5446 | 2.01 |
| 5442 | 1.99 |
| 5439 | 1.98 |
| 5435 | 1.97 |
| 5431 | 1.95 |
| 5427 | 1.94 |
| 5423 | 1.92 |
| 5419 | 1.91 |
| 5415 | 1.89 |

TABLE 3-continued

| cm$^{-1}$ | Absorb. |
|---|---|
| 5412 | 1.88 |
| 5408 | 1.86 |
| 5404 | 1.84 |
| 5400 | 1.83 |
| 5396 | 1.81 |
| 5392 | 1.8 |
| 5388 | 1.78 |
| 5385 | 1.77 |
| 5381 | 1.76 |
| 5377 | 1.74 |
| 5373 | 1.73 |
| 5369 | 1.72 |
| 5365 | 1.72 |
| 5361 | 1.71 |
| 5358 | 1.7 |
| 5354 | 1.7 |
| 5350 | 1.69 |
| 5346 | 1.69 |
| 5342 | 1.68 |
| 5338 | 1.68 |
| 5334 | 1.68 |
| 5331 | 1.68 |
| 5327 | 1.67 |
| 5323 | 1.67 |
| 5319 | 1.67 |
| 5315 | 1.67 |
| 5311 | 1.66 |
| 5307 | 1.66 |
| 5304 | 1.66 |
| 5300 | 1.65 |
| 5296 | 1.65 |
| 5292 | 1.65 |
| 5288 | 1.65 |
| 5284 | 1.64 |
| 5280 | 1.64 |
| 5277 | 1.64 |
| 5273 | 1.64 |
| 5269 | 1.63 |
| 5265 | 1.63 |
| 5261 | 1.62 |
| 5257 | 1.62 |
| 5253 | 1.62 |
| 5250 | 1.61 |
| 5246 | 1.61 |
| 5242 | 1.61 |
| 5238 | 1.6 |
| 5234 | 1.6 |
| 5230 | 1.6 |
| 5226 | 1.6 |
| 5223 | 1.59 |
| 5219 | 1.59 |
| 5215 | 1.59 |
| 5211 | 1.59 |
| 5207 | 1.58 |
| 5203 | 1.58 |
| 5199 | 1.58 |
| 5196 | 1.57 |
| 5192 | 1.57 |
| 5188 | 1.57 |
| 5184 | 1.56 |
| 5180 | 1.56 |
| 5176 | 1.56 |
| 5172 | 1.55 |
| 5169 | 1.55 |
| 5165 | 1.55 |
| 5161 | 1.54 |
| 5157 | 1.54 |
| 5153 | 1.54 |
| 5149 | 1.53 |
| 5145 | 1.53 |
| 5142 | 1.53 |
| 5138 | 1.53 |
| 5134 | 1.52 |
| 5130 | 1.52 |
| 5126 | 1.52 |
| 5122 | 1.52 |
| 5118 | 1.51 |
| 5115 | 1.51 |
| 5111 | 1.51 |
| 5107 | 1.51 |
| 5103 | 1.51 |
| 5099 | 1.51 |
| 5095 | 1.5 |
| 5091 | 1.5 |
| 5088 | 1.5 |
| 5084 | 1.5 |
| 5080 | 1.5 |
| 5076 | 1.49 |
| 5072 | 1.49 |
| 5068 | 1.49 |
| 5064 | 1.49 |
| 5061 | 1.48 |
| 5057 | 1.48 |
| 5053 | 1.48 |
| 5049 | 1.48 |
| 5045 | 1.48 |
| 5041 | 1.48 |
| 5037 | 1.48 |
| 5034 | 1.48 |
| 5030 | 1.47 |
| 5026 | 1.47 |
| 5022 | 1.47 |
| 5018 | 1.47 |
| 5014 | 1.47 |
| 5010 | 1.47 |
| 5007 | 1.47 |
| 5003 | 1.47 |
| 4999 | 1.47 |
| 4995 | 1.47 |
| 4991 | 1.47 |
| 4987 | 1.47 |
| 4983 | 1.47 |
| 4980 | 1.47 |
| 4976 | 1.47 |
| 4972 | 1.47 |
| 4968 | 1.46 |
| 4964 | 1.46 |
| 4960 | 1.45 |
| 4956 | 1.45 |
| 4953 | 1.44 |
| 4949 | 1.44 |
| 4945 | 1.43 |
| 4941 | 1.43 |
| 4937 | 1.42 |
| 4933 | 1.42 |
| 4929 | 1.41 |
| 4926 | 1.41 |
| 4922 | 1.4 |
| 4918 | 1.4 |
| 4914 | 1.39 |
| 4910 | 1.39 |
| 4906 | 1.39 |
| 4902 | 1.38 |
| 4899 | 1.38 |
| 4895 | 1.38 |
| 4891 | 1.38 |
| 4887 | 1.37 |
| 4883 | 1.37 |
| 4879 | 1.37 |
| 4875 | 1.37 |
| 4872 | 1.36 |
| 4868 | 1.36 |
| 4864 | 1.35 |
| 4860 | 1.35 |
| 4856 | 1.35 |
| 4852 | 1.34 |
| 4848 | 1.34 |
| 4845 | 1.33 |
| 4841 | 1.33 |
| 4837 | 1.33 |
| 4833 | 1.32 |
| 4829 | 1.32 |
| 4825 | 1.32 |
| 4821 | 1.32 |
| 4818 | 1.32 |
| 4814 | 1.31 |

TABLE 3-continued

| cm$^{-1}$ | Absorb. |
|---|---|
| 4810 | 1.31 |
| 4806 | 1.31 |
| 4802 | 1.31 |
| 4798 | 1.31 |
| 4794 | 1.31 |
| 4791 | 1.31 |
| 4787 | 1.31 |
| 4783 | 1.31 |
| 4779 | 1.31 |
| 4775 | 1.31 |
| 4771 | 1.31 |
| 4767 | 1.31 |
| 4764 | 1.31 |
| 4760 | 1.31 |
| 4756 | 1.31 |
| 4752 | 1.31 |
| 4748 | 1.3 |
| 4744 | 1.3 |
| 4740 | 1.3 |
| 4737 | 1.3 |
| 4733 | 1.3 |
| 4729 | 1.3 |
| 4725 | 1.3 |
| 4721 | 1.3 |
| 4717 | 1.31 |
| 4713 | 1.31 |
| 4710 | 1.31 |
| 4706 | 1.32 |
| 4702 | 1.33 |
| 4698 | 1.34 |
| 4694 | 1.35 |
| 4690 | 1.36 |
| 4686 | 1.37 |
| 4683 | 1.39 |
| 4679 | 1.41 |
| 4675 | 1.44 |
| 4671 | 1.46 |
| 4667 | 1.48 |
| 4663 | 1.5 |
| 4659 | 1.51 |
| 4656 | 1.53 |
| 4652 | 1.54 |
| 4648 | 1.56 |
| 4644 | 1.57 |
| 4640 | 1.59 |
| 4636 | 1.6 |
| 4632 | 1.61 |
| 4629 | 1.63 |
| 4625 | 1.64 |
| 4621 | 1.66 |
| 4617 | 1.67 |
| 4613 | 1.68 |
| 4609 | 1.69 |
| 4605 | 1.7 |
| 4602 | 1.7 |
| 4598 | 1.7 |
| 4594 | 1.7 |
| 4590 | 1.69 |
| 4586 | 1.68 |
| 4582 | 1.67 |
| 4578 | 1.67 |
| 4575 | 1.66 |
| 4571 | 1.65 |
| 4567 | 1.64 |
| 4563 | 1.64 |
| 4559 | 1.63 |
| 4555 | 1.63 |
| 4551 | 1.63 |
| 4548 | 1.64 |
| 4544 | 1.64 |
| 4540 | 1.65 |
| 4536 | 1.65 |
| 4532 | 1.66 |
| 4528 | 1.67 |
| 4524 | 1.68 |
| 4521 | 1.69 |
| 4517 | 1.7 |
| 4513 | 1.71 |
| 4509 | 1.73 |
| 4505 | 1.74 |
| 4501 | 1.76 |
| 4497 | 1.78 |
| 4494 | 1.8 |
| 4490 | 1.83 |
| 4486 | 1.85 |
| 4482 | 1.88 |
| 4478 | 1.92 |
| 4474 | 1.96 |
| 4470 | 2 |
| 4467 | 2.05 |
| 4463 | 2.11 |
| 4459 | 2.17 |
| 4455 | 2.25 |
| 4451 | 2.35 |
| 4447 | 2.46 |
| 4443 | 2.59 |
| 4440 | 2.76 |
| 4436 | 2.95 |
| 4432 | 3.19 |
| 4428 | 3.47 |
| 4424 | 3.79 |
| 4420 | 4.12 |
| 4416 | 4.45 |
| 4413 | 4.82 |
| 4409 | 5.13 |
| 4405 | 5.19 |
| 4401 | 5.15 |
| 4397 | 5.1 |
| 4393 | 5.05 |
| 4389 | 5.05 |
| 4386 | 5.09 |
| 4382 | 5.2 |
| 4378 | 5.34 |
| 4374 | 5.39 |
| 4370 | 5.2 |
| 4366 | 5.05 |
| 4362 | 5.07 |
| 4359 | 5.26 |
| 4355 | 5.26 |
| 4351 | 5.05 |
| 4347 | 4.98 |
| 4343 | 5.11 |
| 4339 | 5.29 |
| 4335 | 5.32 |
| 4332 | 5.36 |
| 4328 | 5.4 |
| 4324 | 5.28 |
| 4320 | 5.13 |
| 4316 | 4.99 |
| 4312 | 4.95 |
| 4308 | 4.95 |
| 4305 | 4.95 |
| 4301 | 4.95 |
| 4297 | 4.97 |
| 4293 | 5.01 |
| 4289 | 5.06 |
| 4285 | 5.1 |
| 4281 | 5.17 |
| 4278 | 5.37 |
| 4274 | 5.28 |
| 4270 | 5.36 |
| 4266 | 5.34 |
| 4262 | 5.21 |
| 4258 | 5.13 |
| 4254 | 5.15 |
| 4251 | 5.16 |
| 4247 | 5.23 |
| 4243 | 5.21 |
| 4239 | 5.19 |
| 4235 | 5.27 |
| 4231 | 5.24 |
| 4227 | 5.09 |
| 4224 | 5.08 |
| 4220 | 5.19 |
| 4216 | 5.39 |
| 4212 | 5.46 |

TABLE 3-continued

| cm$^{-1}$ | Absorb. |
|---|---|
| 4208 | 5.34 |
| 4204 | 5.23 |
| 4200 | 5.14 |
| 4197 | 5.13 |
| 4193 | 5.1 |
| 4189 | 5.02 |
| 4185 | 5.03 |
| 4181 | 5.07 |
| 4177 | 5.09 |
| 4173 | 5.09 |
| 4170 | 5.14 |
| 4166 | 5.22 |
| 4162 | 5.26 |
| 4158 | 5.27 |
| 4154 | 5.33 |
| 4150 | 5.35 |
| 4146 | 5.29 |
| 4143 | 5.25 |
| 4139 | 5.27 |
| 4135 | 5.34 |
| 4131 | 5.21 |
| 4127 | 5.14 |
| 4123 | 5.07 |
| 4119 | 4.99 |
| 4116 | 4.96 |
| 4112 | 5.02 |
| 4108 | 5.19 |
| 4104 | 5.42 |
| 4100 | 5.49 |
| 4096 | 5.37 |
| 4092 | 5.28 |
| 4089 | 5.2 |
| 4085 | 5.09 |
| 4081 | 5.01 |
| 4077 | 4.97 |
| 4073 | 4.96 |
| 4069 | 4.99 |
| 4065 | 5.02 |
| 4062 | 5.01 |
| 4058 | 5.15 |
| 4054 | 5.36 |
| 4050 | 5.4 |
| 4046 | 5.31 |
| 4042 | 5.2 |
| 4038 | 5.14 |
| 4035 | 5.05 |
| 4031 | 4.95 |
| 4027 | 4.93 |
| 4023 | 5.05 |
| 4019 | 5.23 |
| 4015 | 5.32 |
| 4011 | 5.37 |
| 4008 | 5.14 |
| 4004 | 4.88 |
| 4000 | 4.81 |

We claim:

1. A system for assigning a distillation temperature for a given distillation weight percentage to a fraction of an oil sample based upon near infrared spectroscopy data, the system comprising:
a non-volatile memory device that stores calculation modules and data, the data including NIR spectroscopy data indicative of absorbance values of the crude oil solution for peaks detected in a predetermined wavenumber range for the oil sample;
a processor coupled to the memory;
a first calculation module that calculates and assigns a cumulative and normalized infrared absorbance for the given distillation weight percentage from the data indicative of absorbance values; and
a second calculation module that calculates and assigns a simulated distillation temperature of the fraction as a function of the infrared absorbance for the given distillation weight percentage, and density of the oil sample.

2. The system as in claim 1, wherein the second calculation module calculates and assigns the simulated distillation temperature of the fraction from a multi variable polynomial equation with predetermined constant coefficients developed using linear regression techniques, wherein the variables include the infrared absorbance for the given distillation weight percentage and the density of the oil sample.

3. A system for assigning a distillation temperature for a given distillation weight percentage to a fraction of an oil sample comprising:
a near infrared spectrometer that outputs near infrared spectroscopy data;
a non-volatile memory device that stores calculation modules and data, the data including NIR spectroscopy data indicative of absorbance values of the crude oil solution for peaks detected in a predetermined wavenumber range for the oil sample;
a processor coupled to the memory;
a first calculation module that calculates and assigns a cumulative and normalized infrared absorbance for the given distillation weight percentage from the data indicative of absorbance values; and
a second calculation module that calculates and assigns a simulated distillation temperature of the fraction as a function of the infrared absorbance for the given distillation weight percentage, and density of the oil sample.

4. The system as in claim 3 wherein plural distillation temperatures are assigned to obtain a set of simulated distillation data.

5. The system as in claim 3, wherein the predetermined wavenumber range is 4,000-12,821 cm$^{-1}$.

6. The system as in claim 3, wherein the second calculation module calculates and assigns the simulated distillation temperature of the fraction from a multi variable polynomial equation with predetermined constant coefficients developed using linear regression techniques, wherein the variables include the infrared absorbance for the given distillation weight percentage and the density of the oil sample.

7. The system as in claim 4, wherein the given distillation weight percentage values are 0.5, 5, 10, 20, 30, 40, 50, 60, 70, 80 W %.

8. A method for operating a computer to assign a distillation temperature for a given distillation weight percentage to a fraction of an oil sample based upon near infrared spectroscopy data, the method comprising:
entering into the computer near infrared spectroscopy data indicative of absorbance values of the crude oil solution for peaks detected in a predetermined wavenumber range for the oil sample;
calculating and assigning a cumulative and normalized infrared absorbance for the given distillation weight percentage from the data indicative of absorbance values; and
calculating and assigning a simulated distillation temperature of the fraction as a function of the infrared absorbance for the given distillation weight percentage, and density of the oil sample.

9. The method as claim 8, wherein plural distillation temperatures are assigned to obtain a set of simulated distillation data.

10. The method as claim 8, wherein the predetermined wavenumber range is 4,000-12,821 cm$^{-1}$.

11. The method as in claim 8, wherein calculating and assigning the simulated distillation temperature is with a multi variable polynomial equation with predetermined constant coefficients developed using linear regression techniques, wherein the variables include the infrared absorbance for the given distillation weight percentage and the density of the oil sample.

12. The method as in claim 9, wherein the given distillation weight percentage values are 0.5, 5, 10, 20, 30, 40, 50, 60, 70, 80 W %.

13. A method for assigning assign a distillation temperature for a given distillation weight percentage to a fraction of an oil sample, the method comprising:

obtaining near infrared spectroscopy data indicative of absorbance values of the crude oil solution for peaks detected in a predetermined wavenumber range for the oil sample;

entering into a computer the obtained near infrared spectroscopy data;

calculating and assigning a cumulative and normalized infrared absorbance for the given distillation weight percentage from the data indicative of absorbance values; and calculating and assigning a simulated distillation temperature of the fraction as a function of the infrared absorbance for the given distillation weight percentage, and density of the oil sample.

14. The method as in claim 13 wherein the oil sample is crude oil.

15. The method as in claim 13, wherein the oil sample is obtained from an oil well, stabilizer, extractor, or distillation tower.

16. The method as claim 13, wherein plural distillation temperatures are assigned to obtain a set of simulated distillation data.

17. The method as claim 13, wherein the predetermined wavenumber range is 4,000-12,821 $cm^{-1}$.

18. The method as in claim 13, wherein calculating and assigning the simulated distillation temperature is with a multi variable polynomial equation with predetermined constant coefficients developed using linear regression techniques, wherein the variables include the infrared absorbance for the given distillation weight percentage and the density of the oil sample.

19. The method as in claim 16, wherein the given distillation weight percentage values are 0.5, 5, 10, 20, 30, 40, 50, 60, 70, 80 W %.

* * * * *